(12) United States Patent
Wilson et al.

(10) Patent No.: US 11,160,938 B2
(45) Date of Patent: Nov. 2, 2021

(54) INHALANT DISPENSING SYSTEM AND APPARATUS

(71) Applicant: Loop Laboratories, LLC, Chicago, IL (US)

(72) Inventors: Scott H. Wilson, Chicago, IL (US); Gary Harlan Paulsen, Chicago, IL (US)

(73) Assignee: Loop Laboratories, LLC, Chicago, IL (US)

( * ) Notice: Subject to any disclaimer, the term of this patent is extended or adjusted under 35 U.S.C. 154(b) by 0 days.

(21) Appl. No.: 16/682,548

(22) Filed: Nov. 13, 2019

(65) Prior Publication Data
US 2020/0147325 A1 May 14, 2020

Related U.S. Application Data

(60) Provisional application No. 62/767,367, filed on Nov. 14, 2018.

(51) Int. Cl.
*A61M 15/00* (2006.01)
(52) U.S. Cl.
CPC ........ *A61M 15/009* (2013.01); *A61M 15/002* (2014.02); *A61M 15/008* (2014.02);
(Continued)
(58) Field of Classification Search
CPC ....... A61M 15/00–0085; A61M 15/009–0096; A61M 15/002;
(Continued)

(56) References Cited

U.S. PATENT DOCUMENTS

D207,143 S 3/1967 Goodwin
4,114,811 A 9/1978 Loeffler
(Continued)

FOREIGN PATENT DOCUMENTS

| GB | 2470188 A | * 11/2010 | ......... A61M 15/009 |
| KR | 101504574 | 3/2015 | |
| WO | WO2017093721 | 6/2017 | |

OTHER PUBLICATIONS

International Search Report and Written Opinion for PCT/US2019/060977 dated Mar. 12, 2020, 14 pp.

*Primary Examiner* — Elliot S Ruddie
(74) *Attorney, Agent, or Firm* — Neal, Gerber & Eisenberg LLP

(57) ABSTRACT

An inhalant dispensing system is provided, comprising an inhalant delivery apparatus having a main body, a lower body coupled to the main body and comprising a mouthpiece, and an inhalant delivery mechanism disposed within the main body and configured to deliver an aerosolized solution to the mouthpiece for user inhalation; and a lock out system configured to selectively prevent delivery of the aerosolized solution to the mouthpiece. The inhalant delivery apparatus may be assembled by inserting a portion of the inhalant delivery mechanism into the main body. The lower body may be rotatably coupled to the main body and moveable between a dispensing position and a storage position. The system may be used to control and monitor dosages of a solution contained within a smart canister and administered from the canister via an inhaler, to prevent accidental or unwanted usage of the canister and/or overdosing.

19 Claims, 17 Drawing Sheets

(52) U.S. Cl.
CPC ... *A61M 15/0021* (2014.02); *A61M 2205/276* (2013.01); *A61M 2205/3561* (2013.01); *A61M 2205/52* (2013.01); *A61M 2205/584* (2013.01); *A61M 2205/587* (2013.01); *A61M 2205/6054* (2013.01); *A61M 2205/8206* (2013.01)

(58) Field of Classification Search
CPC ... A61M 15/0021–0026; A61M 2205/27–276; A61M 2205/3561; A61M 2205/52; A61M 2205/584; A61M 2205/587; A61M 2205/6054; A61M 2205/82–8206
See application file for complete search history.

(56) References Cited

U.S. PATENT DOCUMENTS

| | | |
|---|---|---|
| D291,829 S | 9/1987 | Torongo et al. |
| D416,998 S | 11/1999 | Hodson et al. |
| 6,345,617 B1 | 2/2002 | Engelbreth et al. |
| D556,896 S | 12/2007 | Logan |
| 7,383,837 B2 | 6/2008 | Robertson et al. |
| D610,249 S | 2/2010 | Robinson |
| D629,504 S | 12/2010 | Zuyderhoudt |
| D629,507 S | 12/2010 | Zuyderhoudt |
| D629,508 S | 12/2010 | Zuyderhoudt |
| D629,889 S | 12/2010 | Zuyderhoudt |
| D635,658 S | 4/2011 | Warby et al. |
| D657,446 S | 4/2012 | Herfort |
| D657,447 S | 4/2012 | Herfort |
| D681,803 S | 5/2013 | Sheehy |
| D681,804 S | 5/2013 | Sheehy |
| 8,474,448 B2 | 7/2013 | Oi et al. |
| D772,394 S | 11/2016 | Walsh |
| D772,395 S | 11/2016 | Walsh |
| D852,947 S | 7/2019 | Dethlefs et al. |
| D853,555 S | 7/2019 | Oliveras et al. |
| D863,531 S | 10/2019 | Jackson et al. |
| D863,533 S | 10/2019 | Jackson et al. |
| D871,567 S | 12/2019 | Pieters et al. |
| 10,953,168 B2 | 3/2021 | Biswas et al. |
| 10,960,151 B2 | 3/2021 | Weaver et al. |
| 10,967,140 B2 | 4/2021 | Petit |
| 2002/0000225 A1* | 1/2002 | Schuler ............ A61M 15/00 128/200.14 |
| 2003/0098024 A1* | 5/2003 | Hodson ........... A61M 15/0068 128/200.23 |
| 2007/0181120 A1* | 8/2007 | Wright ............ A61M 15/009 128/200.23 |
| 2010/0192946 A1* | 8/2010 | Oi .................. A61M 15/009 128/200.23 |
| 2014/0137862 A1* | 5/2014 | Chen .............. A61M 15/0065 128/203.15 |
| 2016/0217717 A1 | 7/2016 | Lawrence et al. |
| 2018/0361087 A1* | 12/2018 | Howell ........... A61M 15/0023 |
| 2020/0086069 A1* | 3/2020 | Riebe ............. A61M 15/009 |
| 2020/0376209 A1* | 12/2020 | Mohammed ....... A61M 15/002 |
| 2020/0384216 A1* | 12/2020 | Eicher ............ B05B 11/3091 |

* cited by examiner

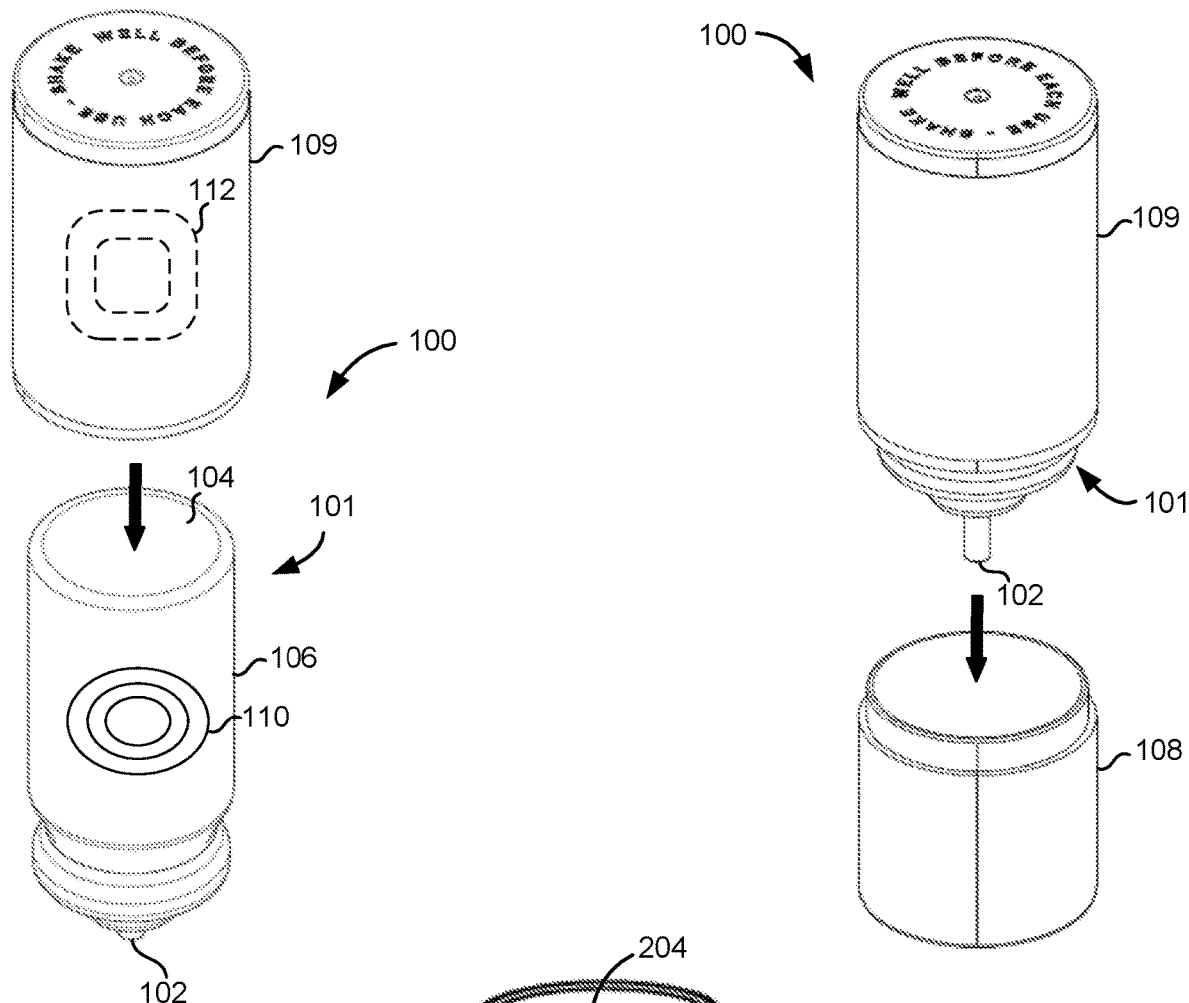
FIG. 1A
FIG. 1B
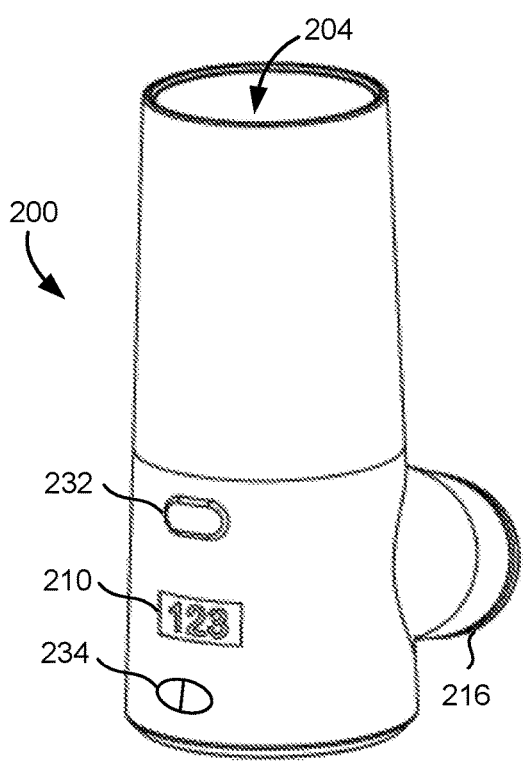
FIG. 3

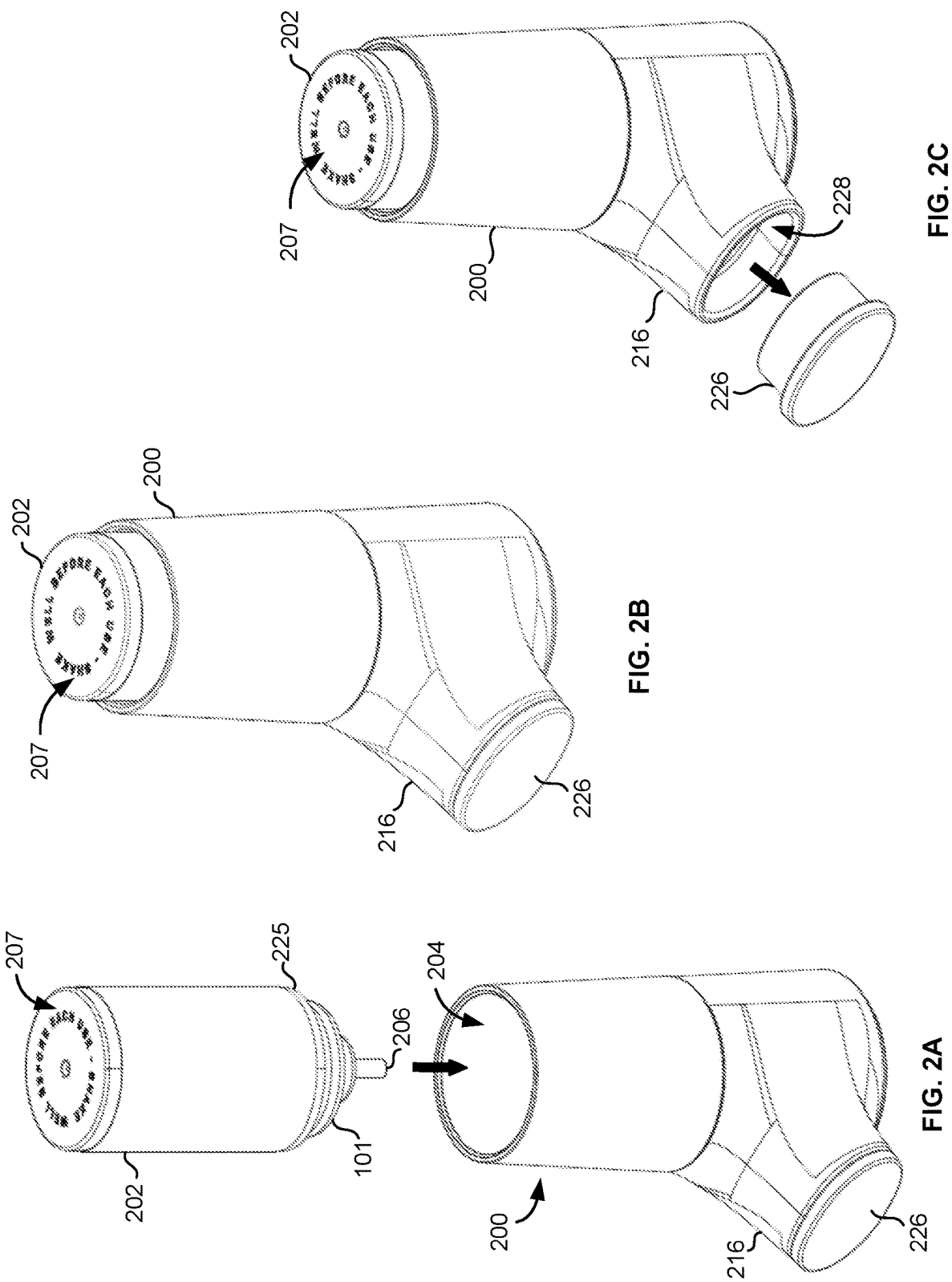

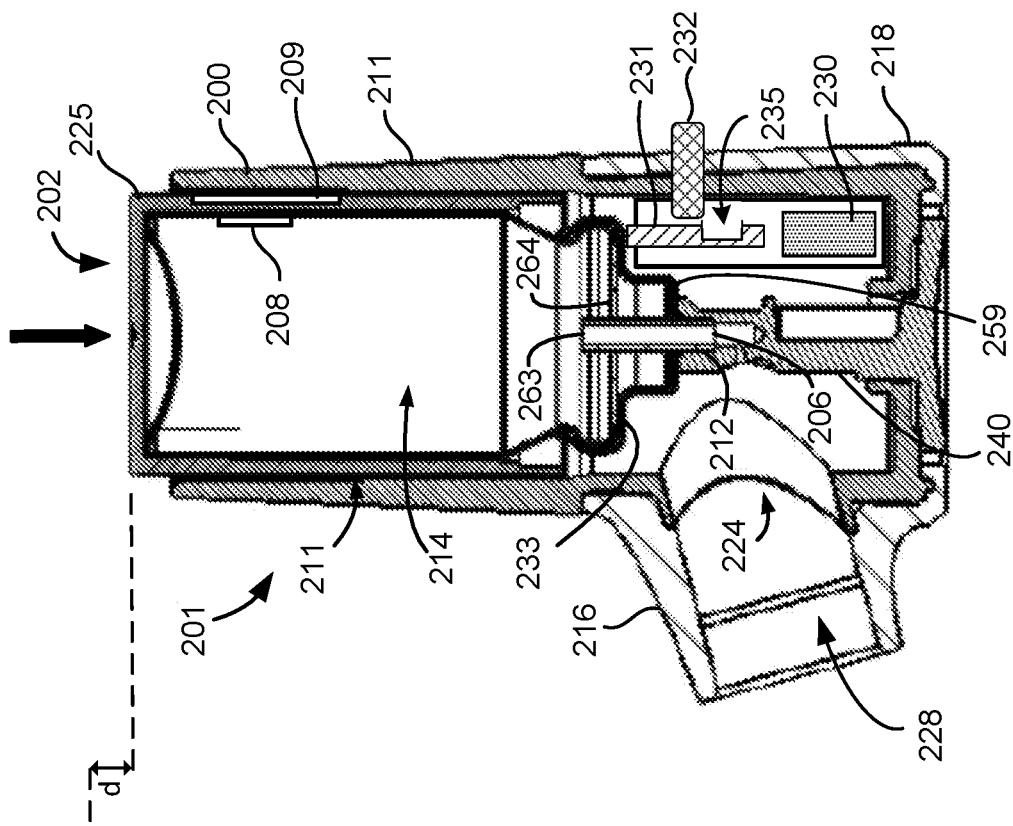
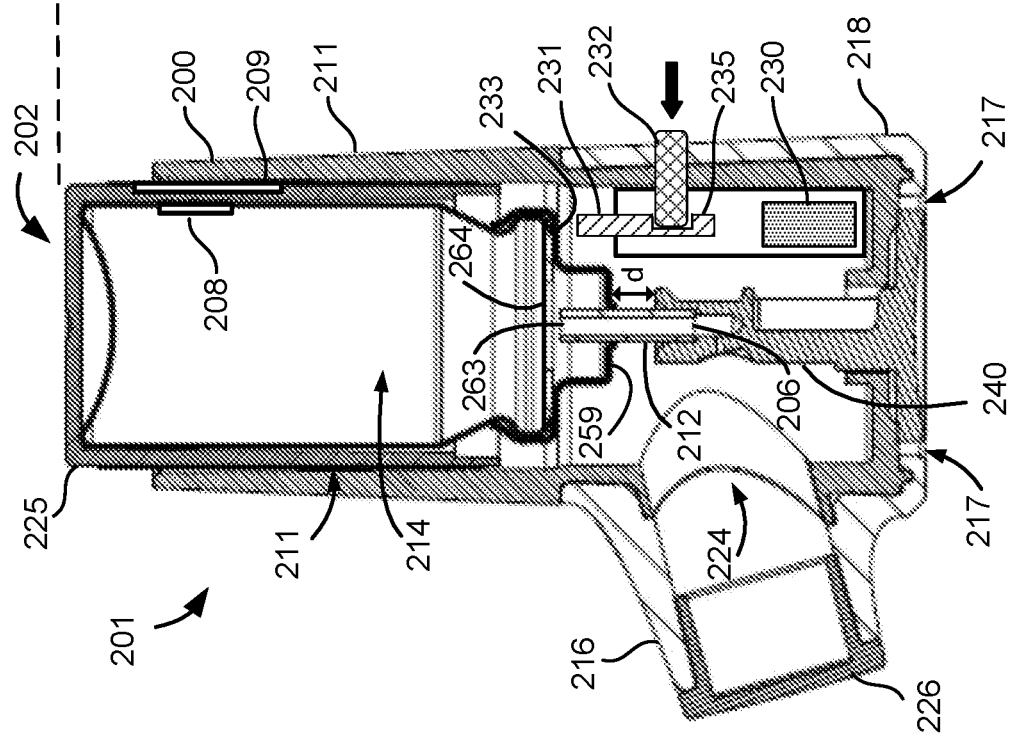
FIG. 4A
FIG. 4B

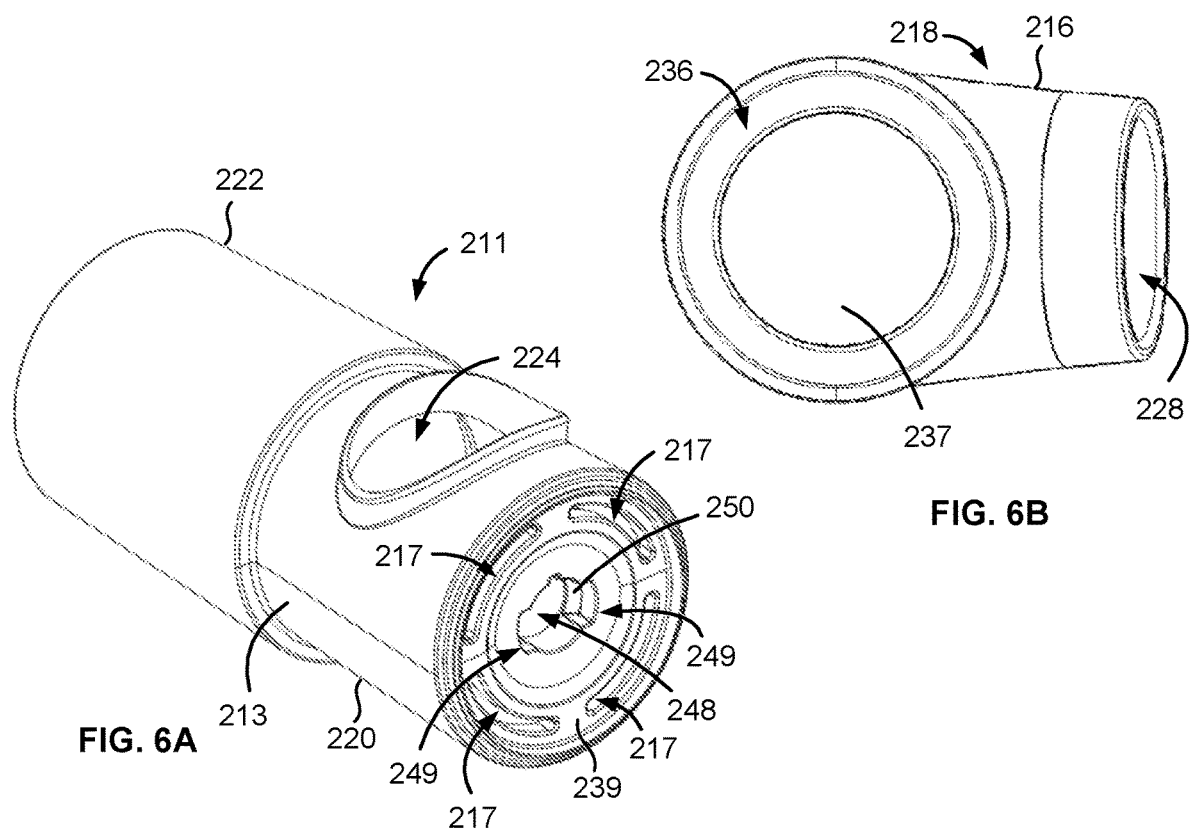
FIG. 6A
FIG. 6B
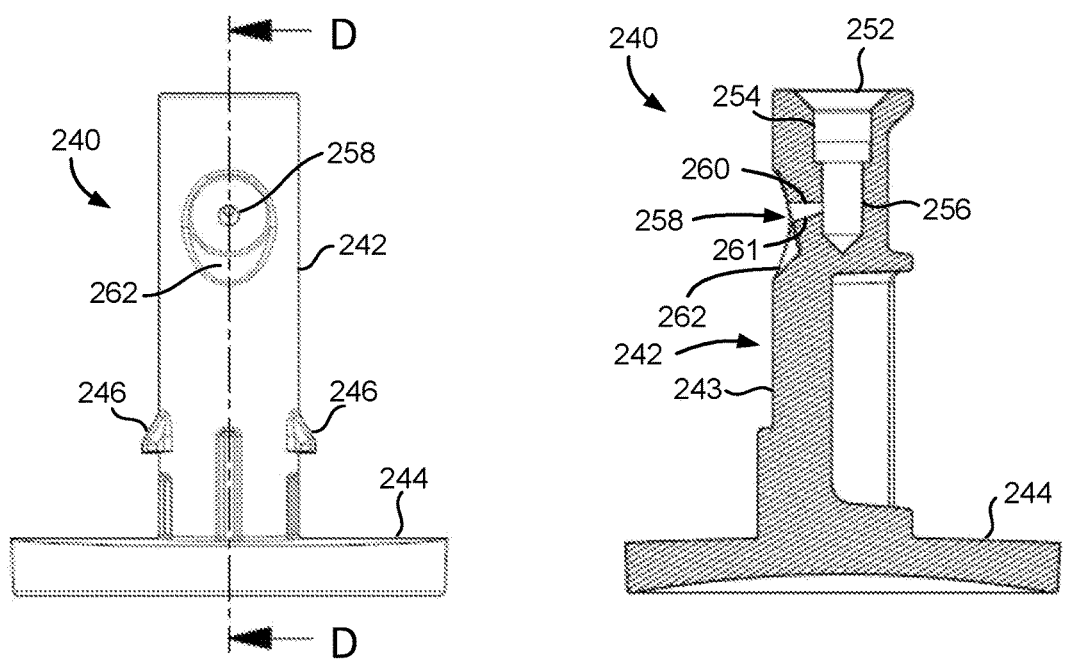
FIG. 6C
FIG. 6D

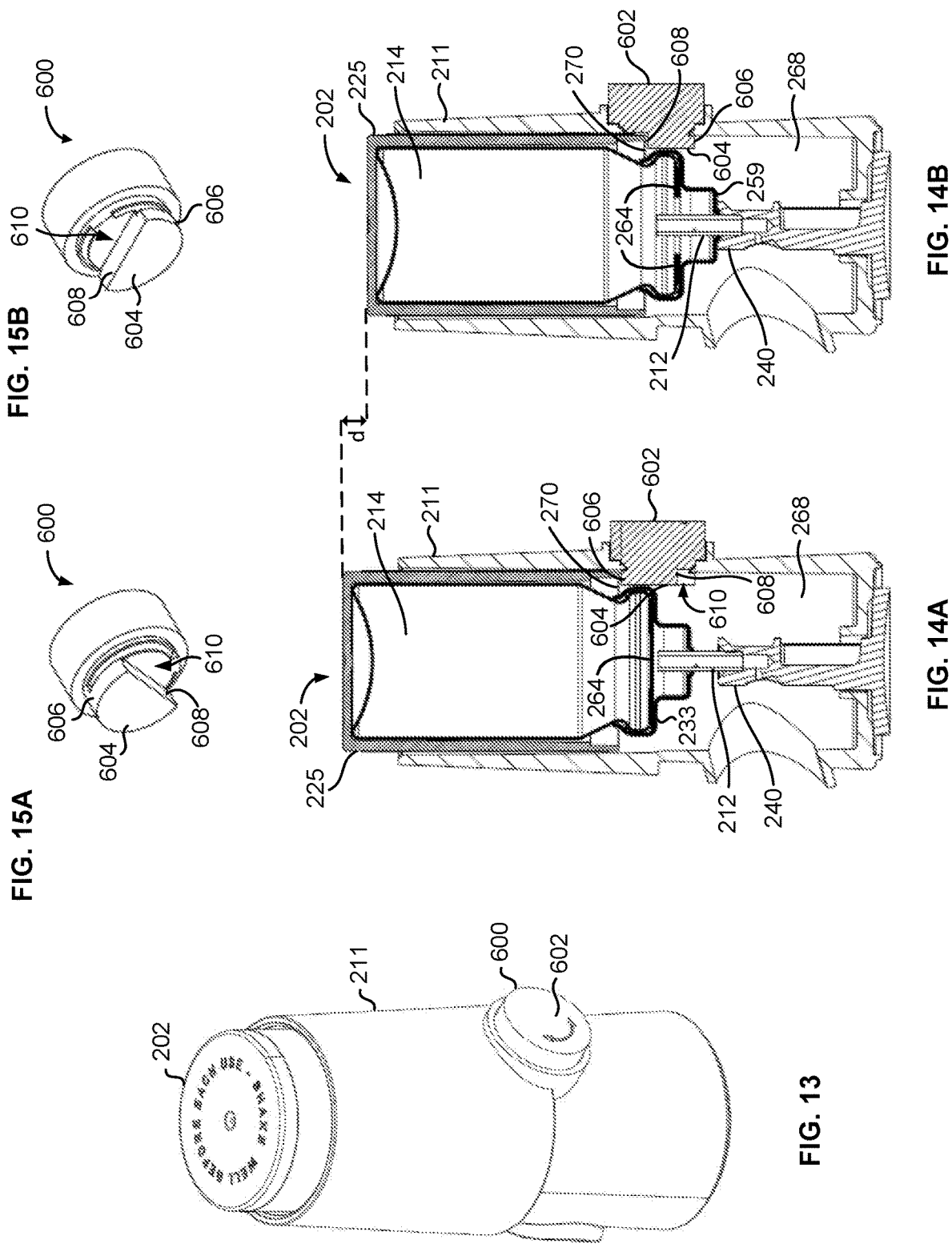

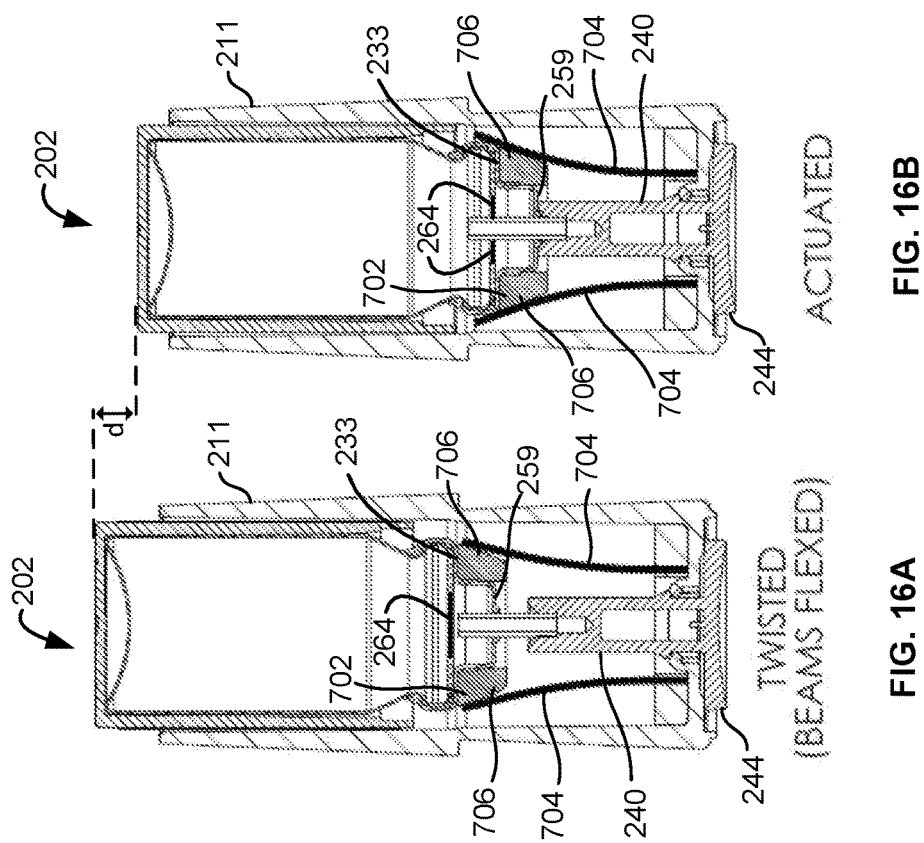
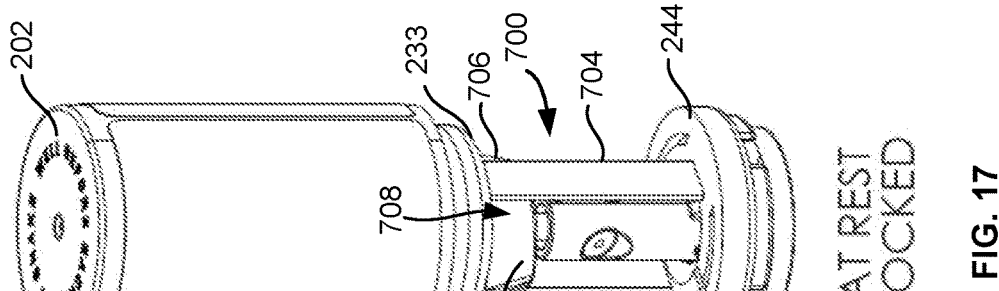
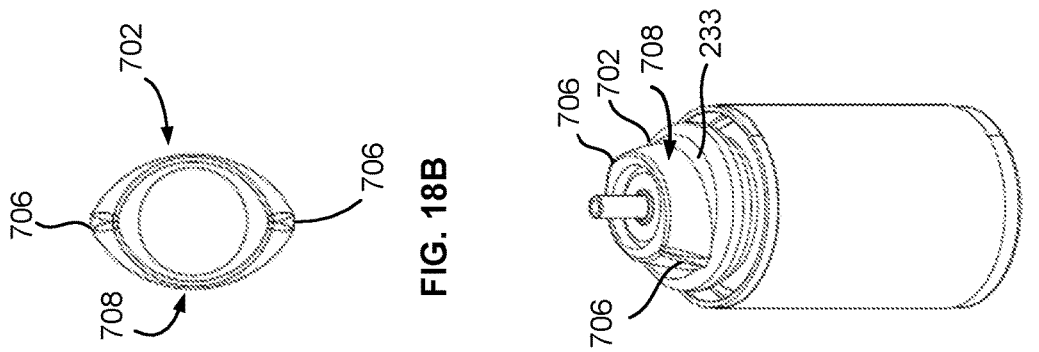

INHALANT DISPENSING SYSTEM AND APPARATUS

CROSS-REFERENCE TO RELATED APPLICATIONS

This application claims the benefit of U.S. Provisional Patent Application No. 62/767,367, filed on Nov. 14, 2018, the contents of which are incorporated herein by reference in their entirety.

TECHNICAL FIELD

The present invention relates to inhalant dispensers, including apparatus for administering an inhalant and systems for controlling and monitoring administration of the inhalant.

BACKGROUND

There are various forms of inhalers used to administer medicine or other substances to the lungs. Typically, these involve a solution in a pressurized canister, a dispensing actuator, and a rudimentary metering valve that controls the amount of solution released when activated. But this amount is imprecise, and the inhaler will dispense each time there is actuation, with no measurement or controls in place. One form of inhaler is a nebulizer, which breaks up a liquid solution into a mist as it is being dispensed. This may be done in various ways, such as by using ultrasonic waves, air pressure (an atomizer), or a heating element.

With the recent growth in vaping and legalization of certain *cannabis*-based products, inhalers are becoming commonplace, and are not necessarily used for medicinal purposes. Common devices can be loaded with a cartridge containing an aerosol solution, which is then inhaled over time and the user disposes the empty cartridge when done. Meanwhile, the device is re-used. However, there is no telling specifically what chemicals or substances are in the cartridges, and there are no controls or monitoring over the rate or amount of solution dispensed. This presents a serious chance for abuse of the inhalant, particularly as it becomes more frequent to use inhalants for non-medicinal purposes.

SUMMARY OF THE INVENTION

Embodiments of the present invention include an intelligent inhalant system comprised of an inhalant device, or inhaler, designed to receive a smart canister that contains a solution to be dispensed. Each canister contains specific information about the solution content, and may also contain dosing information that may be specific to the solution. The canister may also contain information specific to the user of the system, which may be combined with the solution information to make dosing and administration decisions. The dispensing device works in association with the smart canister to control dosing of the solution, provide the user with various information about the solution, and monitor the user's inhalant consumption over time.

The inhalant dispensing device or inhaler, itself, may be implemented using one or more embodiments, or a combination thereof. Embodiments can include various safety and other use-related features, such as, for example, a child lock system configured to prevent removal of the canister from the inhaler by a child, a dosage administration system configured to electronically monitor dosing and prevent excessive dosing, and an identification system configured to identify the canister being used and provide dosage information associated therewith. Some embodiments include a preparation system configured to monitor preparation of the solution (e.g., through shaking) and provide an indication when the solution is ready for use. One or more features may require the use of wireless communication with a personal electronic device, such as, e.g., a smartphone. Embodiments also include various physical configurations for the inhaler, each configuration being designed to house one or more of the above systems. One example embodiment includes a twist feature that enables the inhaler to be turned or twisted from an upright position, better suited for storage, to an angled position, better suited for use of the inhaler. Another example embodiment has a more curved shape overall with air vents integrated into opposite sidewalls of the inhaler, while yet another example embodiment has a more conical or angular shape with a flat bottom and a circular air vent integrated into the bottom surface.

While certain features and embodiments are referenced above, these and other features and embodiments of the present invention will be, or will become, apparent to one having ordinary skill in the art upon examination of the following figures and detailed description. It is intended that all such additional embodiments and features included within this description, be within the scope of the present invention, and be protected by the accompanying claims.

BRIEF DESCRIPTION OF THE DRAWINGS

The present invention can be better understood with reference to the following drawings. The components in the drawings are not necessarily to scale, emphasis instead being placed upon clearly illustrating the principles of the present invention. In the drawings, like reference numerals designate corresponding parts throughout the several views.

FIGS. 1A and 1B are partially exploded, perspective views of an exemplary smart canister in accordance with certain embodiments.

FIG. 2A is a front perspective view of an exemplary inhalant dispenser and the smart canister of FIG. 1B exploded above the dispenser, in accordance with certain embodiments.

FIG. 2B is a front perspective view of the inhalant dispenser of FIG. 2A with the smart canister installed therein, in accordance with certain embodiments.

FIG. 2C is a partially exploded, front perspective view of the inhalant dispenser of FIG. 2B, in accordance with certain embodiments.

FIG. 3 is rear perspective view of the inhalant dispenser of FIG. 2A, in accordance with certain embodiments.

FIG. 4A is a lengthwise cross-sectional view of an exemplary inhalant dispensing system, in accordance with certain embodiments.

FIG. 4B is a lengthwise cross-sectional view like FIG. 4A, except showing the inhalant dispensing system in a dispensing position, in accordance with certain embodiments.

FIG. 6A is a side perspective view of an actuator housing portion of the inhalant dispenser assembly shown in FIG. 5, in accordance with certain embodiments.

FIG. 6B is a bottom view of a mouthpiece portion of the inhalant dispenser assembly shown in FIG. 5, in accordance with certain embodiments.

FIG. 6C is a close-up, side view of an actuator portion of the inhalant dispenser assembly shown in FIG. 5, in accordance with certain embodiments.

FIG. 6D is a lengthwise cross-sectional view of the actuator portion shown in FIG. 6C, in accordance with certain embodiments.

FIG. 13 is a perspective view of an exemplary inhalant dispenser with a first lockout system and an exemplary canister installed therein, in accordance with certain embodiments.

FIGS. 14A and 14B are lengthwise cross-sectional views of the inhalant dispenser of FIG. 13 while the first lockout system is in locked and unlocked orientations, respectively, in accordance with certain embodiments.

FIGS. 15A and 15B are close-up, perspective views of an exemplary knob of the first lockout system in the locked and unlocked orientations, respectively, in accordance with certain embodiments.

FIGS. 16A and 16B are lengthwise cross-sectional views of an exemplary inhalant dispenser with a second lockout system and an exemplary canister installed therein, with the second lockout system being shown in a flexed state and an actuated state, respectively, in accordance with certain embodiments.

FIG. 17 is a perspective view of the second lockout system coupled to the inhalant dispenser and canister of FIGS. 16A and 16B, but with portions of the inhalant dispenser removed and the second lockout system in a locked position, in accordance with certain embodiments.

FIG. 18A is a perspective view of an exemplary canister coupled to an exemplary collar of the second lockout system, in accordance with certain embodiments.

FIG. 18B is a close-up, top view of the collar shown in FIG. 18A, in accordance with certain embodiments.

DETAILED DESCRIPTION

The description that follows describes, illustrates and exemplifies one or more particular embodiments of the present invention in accordance with its principles. This description is not provided to limit the invention to the embodiments described herein, but rather to explain and teach the principles of the invention in such a way to enable one of ordinary skill in the art to understand these principles and, with that understanding, be able to apply them to practice not only the embodiments described herein, but also other embodiments that may come to mind in accordance with these principles. The scope of the present invention is intended to cover all such embodiments that may fall within the scope of the appended claims, either literally or under the doctrine of equivalents.

Figure 5:
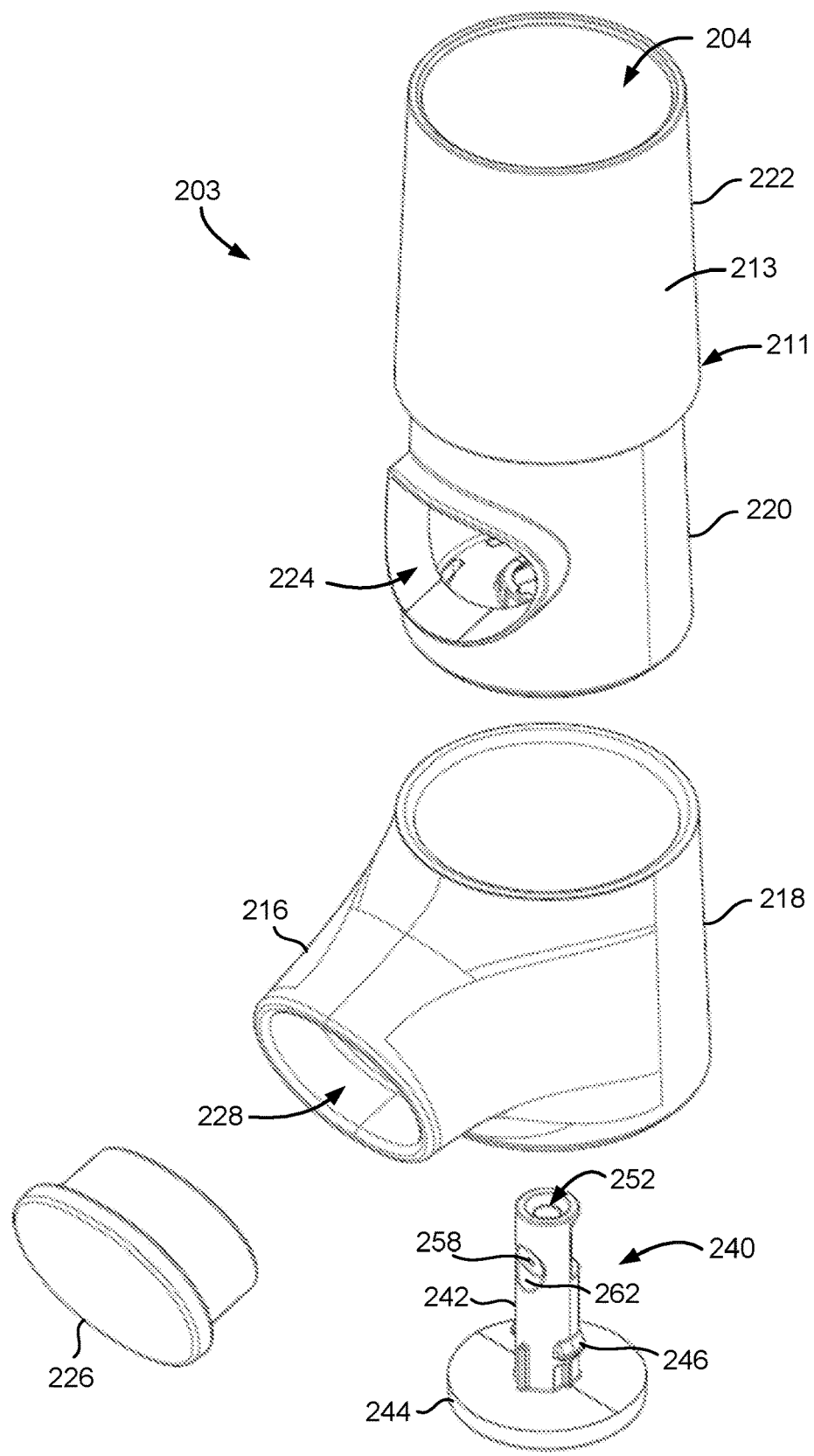
FIG. 5 is an exploded, perspective view of an exemplary inhalant dispenser assembly, in accordance with certain embodiments.

FIGS. 1A and 1B illustrate an exemplary smart canister 100 configured for installation into an inhaler (not shown). The term "smart" is used to denote that the canister 100 has at least data available for interpretation and in some cases, a memory stored thereon. The smart canister 100 includes a cartridge portion 101 (or "cartridge") for storing a substance or solution to be aerosolized. Though other shapes could be employed, the illustrated cartridge 101 is cylindrical in shape, having an opening or nozzle 102 for dispensing an aerosol at a first end, and a solid top surface 104 at an opposing second end. The majority of the length between the opening 102 and the top surface 104 comprises a solution compartment 106 of the cartridge 101, in which a solution is housed or stored before being converted to an aerosol for delivery. This conversion function may be performed by a converter or actuator (e.g., as shown in FIG. 5). A removable cap 108 may be used to cover the opening 102 when the canister 100 is not installed into an inhaler, or is otherwise not in use.

In embodiments, the canister 100 further includes a top cap 109, or sleeve, that slides over the top surface 104 of the cartridge 101 and extends down over all or most of the solution compartment 106, for example, as shown in FIG. 1B. In some embodiments, the top cap 109 is removable and reusable with other cartridges, as described below. In other embodiments, the top cap 109 is permanently attached to the cartridge 101 using a press-fit mechanism, such as, for example, a plurality of crush ribs disposed on the interior surface of the top cap 109. In some cases, the top cap 109 may be sized so that an overall size (e.g., diameter and/or length) of the canister 100 is larger than that of traditional canisters containing medicinal solutions (e.g., for treating asthma and other respiratory issues), so that the canister 100 cannot be used with conventional inhalers for administering medicine. Such embodiment may be preferred to help differentiate the canister 100 from existing medicinal canisters, and to prevent accidental or unauthorized use of the canister 100 with a conventional inhaler by, for example, children or minors.

FIGS. 2A-2C and FIG. 3 illustrate an exemplary inhalant dispenser 200 (also referred to herein as an "inhaler" or "inhalant delivery apparatus") configured to receive a smart canister 202, similar to the canister 100 shown in FIG. 1. As shown, the canister 202 is inserted into an open top 204 of the inhaler 200 with a dispensing end 206 (similar to opening 102 shown in FIG. 1A) of the canister 202 being inserted first. During use, a top end 207 of the canister 202 is pressed downwards, forcing the canister 202 further into the inhaler 200 and triggering an inhalant delivery mechanism disposed inside the inhaler 200 (e.g., valve actuator 240 shown in FIG. 5). The inhalant delivery mechanism can be configured to convert the canister solution to aerosol and dispense the aerosol through an open end 228 of a mouthpiece 216 of the inhaler 200. In embodiments, the inhaler 200 may be configured as a metered-dose inhaler (MDI) that delivers a specific amount or quantity of solution (e.g., medication or other substance) to the lungs in the form of a short burst of aerosolized solution, which is administered to the user via inhalation. While FIGS. 2-7 show a particular form for the inhaler 200, the smart canister 202 can be installed in any inhalant device that provides a comfortable holding interface for the user and may take other forms, for example, as shown in FIGS. 8-12.

Referring back to FIG. 1A, in embodiments, the cartridge 101 included in the smart canister 100/202 can be a "smart cartridge" that includes a smart label 110 comprising data related to the solution residing inside the cartridge 101. The data may include product information that identifies the exact solution loaded inside the canister, including strain, formulation, and/or blend information (e.g., CBD levels, THC levels, etc.), product preparation information (e.g., mixing requirements, etc.), and/or usage information, including how many doses have been administered and/or are left in the canister 100. In some embodiments, the smart label 110 may be implemented as or in an adhesive sticker, decal, or other type of printed product that can be attached to the cylindrical body of the canister 100 and has certain information (e.g., brand name, brand logo, product name, etc.) printed on its front surface. In such cases, the electronic component of the smart label 110 may be embedded within the adhesive/printed product. In other cases, the smart label 110 may be attached directly to the canister body, for example, as shown in FIG. 1A.

The smart label 110 may include, for example, a radio frequency identification (RFID) tag or a near-field communication (NFC) tag that is readable by a corresponding data receiver 112 (e.g., RFID or NFC reader) included inside the inhaler 200 or in the top cap 109 coupled to the cartridge 101, as shown in FIGS. 1A, 4A and 4B. The smart label 110 may enable tracking of the contents of the cartridge 101 and usage thereof and may help with ordering or re-ordering of cartridges from the supplier once the product levels are low. For example, usage data collected via the smart label 110 may be used by the supplier to discover which cartridges or canisters are being used more frequently and make recommendations for future orders based on use patterns. As will be appreciated, other types of short-range wireless communication technology and/or data storage device may be used to store product or solution information on the canister 100 and transfer the stored information to the inhaler 200 or other component for identification, monitoring, and tracking purposes.

Referring back to FIG. 3, the inhaler 200 may further include a counter 210 for visually keeping track of the number of doses that have already been administered from the canister 202, or the number of doses remaining in the canister 202. The counter 210 may reset each time the canister is changed, or may be updated to reflect the dosage information associated with the canister 202 installed in the inhaler 200. In embodiments, the counter 210 may have a digital output that is electronically controlled by the canister 202 or other component of the inhaler 200.

FIGS. 4A and 4B are cross-sectional views of an exemplary inhalant dispensing system 201, taken down its longitudinal centerline, in accordance with embodiments. The system 201 comprises the inhaler 200 and the canister 202 installed within a main body 211 of the inhaler 200. As shown, the dispensing end 206 of the canister 202 is connected to a dispensing tube 212 that leads into a solution compartment 214 of the canister 202 for storing a solution or substance to be inhaled (e.g., similar to solution compartment 106). When a user gives an indication that a dosage is requested (such as, e.g., by pressing a button on the inhaler 200 or by pressing down on the canister 202), a metered amount or dose of the solution may be dispensed from the solution compartment 214 through the dispensing end 206. In some embodiments, the solution contains a liquid suspension comprised of small particles (e.g., tiny liquid drops) suspended in a gas (e.g., air), and the solution compartment 214 can be configured to store the solution in a highly pressurized state. The solution may also be rendered in other forms, as will be appreciated.

The inhaler 200 includes an inhalant delivery mechanism, or converter, for converting the dose of solution into aerosol and dispensing the aerosolized solution towards the mouthpiece 216 of the inhaler 200. In some embodiments, the inhalant delivery mechanism includes a valve actuator 240 configured to cause a pressure drop in the dose of solution, for example, where the solution is a liquid suspension under pressure, thus rendering the suspended liquid into an aerosolized solution. In other embodiments, the converter may include a heating element to aerosolize the solution, or employ other known techniques for converting from solution to mist (such as, e.g., an atomizer, vibration generator, or ultrasonic wave generator).

FIGS. 5 through 6D illustrate an exemplary inhalant dispenser assembly 203 (also referred to herein as "inhaler assembly") for building or forming the inhaler 200, in accordance with embodiments. As shown in FIG. 5, the inhaler assembly 203 includes a main body 211 (also referred to as "actuator housing") with a generally cylindrical shape and hollow interior or cavity formed by sidewall 213. As shown in FIG. 6A, the sidewall 213 extends from the open top 204 to a bottom surface 239 of the main body 211. In some embodiments, the main body 211 may extend along, or constitute, the entire length of the inhaler 200, or at least a substantial portion thereof.

A lower chamber 220 of the main body 211 is configured (e.g., sized and shaped) for coupling to a lower body 218 of the inhaler assembly 203 and for receiving the valve actuator 240, or at least a substantial portion thereof. An upper chamber 222 of the main body 211 defines the open top 204 for receiving the canister 202 and is sized and shaped to house the canister 202 therein during use. In embodiments, the main body 211 and the lower body 218 may be configured to form a smooth or flush outer surface once the two are joined together. For example, as shown, the lower chamber 220 may have a smaller diameter than the upper chamber 222, while at least a top region of the lower body 218 may have a diameter that is substantially similar to the diameter of the upper chamber 222. As a result, the external surface of the upper chamber 222 may be flush with the external surface of the lower body 218 once the lower chamber 220 is coupled within the lower body 218.

As shown in FIGS. 5 and 6A, the lower chamber 220 includes an aperture 224 within the sidewall 213 of the main body 211 to allow the aerosolized solution to exit the lower chamber 220 and flow directly into the mouthpiece 216. For example, the mouthpiece 216 may be shaped as a tube with two open ends, the external open end 228 and an opposing internal open end disposed towards the valve actuator 240. The aperture 224 may be aligned with the internal open end of the mouthpiece 216 and may be sized and shaped to match a diameter of the internal open end and/or may be coupled to the internal end of the mouthpiece 216. As a result, aerosol dispensed from the valve actuator 240 can flow directly into the mouthpiece 216 via the aperture 224 and out the external open end 228 towards the user. As shown, the mouthpiece 216 may extend out at an angle from a side wall of the lower body 218 to advantageously position the mouthpiece 216 towards the user for inhalation purposes.

The open end 228 of the mouthpiece 216 may be covered by a dust cap 226 when the inhaler 200 is not in use, and uncovered during use to allow the aerosolized solution to exit the inhaler 200. In embodiments, the lower body 218 (also referred to as "silicone boot") can be made of silicone or other somewhat flexible material to provide a comfortable surface for engaging the user's mouth and/or to allow the dust cap 226 to be easily secured to and removed from the mouthpiece 216, for example, using a press-fit attachment. In some embodiments, the dust cap 226 itself may be made of a hard plastic material, to further facilitate this feature.

In embodiments, the main body 211 may be a single unit made of hard plastic, for example, using injection molding techniques, and the silicone boot 218 may be stretched over the lower chamber 220 of the main body 211 in order to secure the silicone boot 218 to the main body 211, for example, using a tight-fit attachment. The main body 211 may be permanently attached to the lower body 218 once assembled in this manner. In other cases, the lower body 218 may be formed onto or around the main body 211 using an overmolding procedure or other similar manufacturing technique.

The inhaler 200 can include a plurality of air vents 217 to allow for proper air flow through the inhaler 200 during use. The air vents 217 may be formed into a bottom surface 239 of the main body 211, as shown in FIG. 6A. The lower body 218 may include a circular opening 236, as shown in FIG. 6B, that corresponds to the locations of the air vents 217, such that after assembly of the inhaler 200, the air vents 217 are not blocked by the lower body 218. Likewise, the valve actuator 240 may be configured to sit within a center area 237 that is surrounded by the air vents 217, so as to not inhibit air flow through the air vents.

FIGS. 6C and 6D are close-up and cross-sectional views, respectively, of the valve actuator 240, in accordance with embodiments. The value actuator 240 may be coupled to the lower body 218 of the inhaler assembly 203 and once assembled therein, may be permanently attached to the lower body 218 (see, e.g., FIGS. 4A and 4B). As shown, the valve actuator 240 includes an elongated tube or post 242 extending up from, or substantially perpendicular to, a base plate 244 and having one or more flanges or snap-locks 246 formed onto, and extending out from, a sidewall 243 forming the post 242. During assembly, the post 242 may be inserted through an aperture 248 formed in the bottom surface 239 of the lower chamber 220 in order to couple the valve actuator 240 to the main body 211.

More specifically, in the bottom surface 239 of the main body 211, one or more recesses 249 are disposed directly adjacent to the aperture 248, so that the aperture and the rear-facing open ends of the recesses 249 form a single opening, as shown in FIG. 6A. Each recess 249 also includes a solid wall 250 on an interior side of the recess 249, opposite the rear-facing open ends and towards the upper chamber 222. The recesses 249 are configured (e.g., sized and shaped) to receive respective flanges 246 of the post 242 up until the walls 250. The walls 250 are configured to press the flanges 246 and corresponding portion of the sidewall 243 inwards as the valve actuator 240 passes through the aperture 248. In embodiments, the sidewall 243 may be made of plastic, a hard rubber or other resilient material capable of flexing or collapsing inward enough to allow the flanges 246 and sidewall 243 to pass through the aperture 248 and also capable of springing back to a neutral position once the flanges 246 clear the walls 250. In some cases, additional upward pressure may be applied to the valve actuator 240 to force the flanges 246 past the walls 250 of the recesses 249 and through the aperture 248. As shown, the flanges 246 may be sloped to enable the flanges 246 to slide upwards and against the walls 250 as the sidewall 243 flexes inwards. The flanges 246 may also be biased outward, such as with a spring.

According to embodiments, the valve actuator 240 (also referred to as an "inhalant delivery mechanism") may be configured to dispense a measured amount, or dose, of aerosolized solution into the mouthpiece 216 in response to downward actuation of the canister 202, for example, as shown in FIG. 4B. As illustrated in FIG. 6D, the valve actuator 240 includes an opening 252 at a top end of the post 242 for receiving the dispensing tube 212 of the canister 202. The top opening 252 is connected to an internal channel 254 configured to receive at least a portion of the dispensing tube 212 of the canister 202 inside the post 242, once the canister 202 is fully installed in the inhaler 200, as shown in FIG. 4A. The channel 254 is coupled to an expansion chamber 256 disposed within the post 242 to hold the dose of solution dispensed from the canister 202, for example, in response to a downward actuation of the canister 202. The actuator post 242 also includes an orifice or nozzle 258 coupled to the expansion chamber 256 and configured to allow the aerosolized solution to exit the expansion chamber 256, once actuation is complete.

More specifically, in FIG. 4A, the canister 202 is shown in a neutral position, wherein a base end 259 of the canister 202 is a distance d away from the top end of the valve actuator 240. In FIG. 4B, the canister 202 is shown in a dispensing position, or actuated position, wherein the canister 202 is displaced downwards by the same distance d, or until the base end 259 is resting against or in contact with the valve actuator 240. As the canister 202 moves downwards, the dispensing end 206 of the dispensing tube 212 is held in place by the internal channel 254 of the valve actuator 240. This causes an opposite end 263 of the dispensing tube 212 to be temporarily pushed into, or placed in communication with, the solution compartment 214, thus sending a dose of solution into the dispensing tube 212. For example, the solution compartment 214 may include a movable barrier 264 configured to keep the solution within the solution compartment 214 when the canister 202 is not actuated and further configured to receive, or allow entry of, the opposite end 263 of the tube 212 when the canister 202 is actuated. In some cases, a threshold amount of force (e.g., due to the downward displacement of the canister 202) may be required to push the tube end 263 through the barrier 264, or otherwise cause the barrier 264 to receive the tube 212. The moveable barrier 264 may be configured in any suitable form, including, for example, a pair of dispensing doors configured to slide open to allow passage of the tube 212 there through and/or a flexible membrane or one-way valve configured to accept insertion of the tube 212.

Once the dispensing tube 212 is in communication with the solution compartment 214, the solution travels into the expansion chamber 256 and ultimately, out the nozzle 258 of the valve actuator 240. In embodiments, the solution may still be in a pressurized liquid form when dispensed into the expansion chamber 256, but as the solution exits the nozzle 258, the pressure of the solution drops, or is released, thus causing the liquid suspension to become an aerosol. In some embodiments, a size or volume of the expansion chamber 256 may be selected based on an expected dosage amount, or the volume of solution that makes one dose. In some embodiments, the volume of the expansion chamber 256 may be increased, or decreased, to accommodate larger, or smaller, dosages, for example, during manufacturing.

In embodiments, the nozzle 258 may be configured to aim the aerosol downwards and align the direction of the aerosol spray with the angle of the mouthpiece 216, as shown in FIG. 4A. For example, as shown in FIG. 6D, an upper surface 260 of the nozzle 258 may be substantially horizontal and a lower surface 261 of the nozzle 258 may be angled or sloped downwards, thus directing the aerosol to spray downwards. In addition, an exterior surface 262 adjacent the nozzle 258 may also be sloped or angled downwards to form a cone-shaped recess on the post 242, just below the nozzle 258, as shown in FIG. 5. The cone-shaped recess 262 may also be configured to aim the aerosol downwards and directly into the mouthpiece 216. In embodiments, a size of the nozzle 258 may be selected to control the pressure drop created and/or the rate of aerosolization.

Referring back to FIG. 2A, the smart canister 202 shown in the featured embodiment is generally cylindrical in shape and is comprised of a base end, or dispensing end 206, and a top end 207. The canister 202 includes a top cap 225, similar to top cap 109 shown in FIG. 1A, that is also cylindrical in shape and is designed to fit reasonably snugly over, for example, the top surface 104 of the cartridge 101 shown in FIG. 1A, to prevent the cartridge 101 from falling out of the top cap 225, for example, when the canister 202 is turned upside down for insertion into the inhaler 200. In some embodiments, the top cap 225 can be twisted onto one or more threaded extensions (not shown) protruding from a sidewall of the upper chamber 222 of the inhaler's main body 211 in order to secure the canister 202 to the inhaler 200.

While the cartridge 101 is designed to be disposable once the solution has been dispensed, the top cap 225 can be removable and reusable with other cartridges. In some cases, the top cap 225 may be loaded with information specific to the user/owner of the top cap 225. In some cases, the top cap 225 can also house information about the solution contained within the smart cartridge 101. In some embodiments, the top cap 225 includes a data receiver 209 (e.g., RFID or NFC reader), similar to the reader 112 shown in FIG. 1A, to read or retrieve the information stored on a memory device 208

(e.g., RFID tag or NFC chip) included on the cartridge 101, similar to the smart label 110 shown in FIG. 1A. In one embodiment, the top cap 225 is in electronic communication with the converter of the inhaler 200 and controls the opening of dispensing doors coupled to the converter, operation of the heating element, and/or other component in order to control whether and how much solution is dispensed from the inhaler 200.

The top cap 225 may also record dosage information associated with the canister 202 and/or the cartridge 101 into a memory chip, such as the amount of solution dispensed and the time it was dispensed. This information may be communicated to the counter 210 to provide accurate dosage counts. Storing the dosage information in the top cap 225 enables the information to travel with the top cap 225 and cartridge 101 coupled thereto, such that upon placement of the canister 202 in a new inhaler, the counter of the new inhaler can be automatically updated to reflect an accurate dosage count for that canister 202.

As shown in FIGS. 4A and 4B, the inhalant dispensing system 201 further includes an electronics module 230 embedded within the lower body 218 of the inhaler 200. The electronics module 230 may be configured to enable monitoring, tracking, dosing, and/or communication features, in accordance with embodiments. The electronics module 230 may be in electronic communication with the top cap 225 of the canister 202 and/or the data receiver 209 included in the top cap 225, in order to obtain information stored in the memory device 208 about the canister 202, the cartridge 101 included therein, and/or the owner of the top cap 225. In some embodiments, the electronics module 230 may also be in wireless communication with a software application that presents a user interface to the user, such as, e.g., on a smartphone, tablet, or other computer device, or to a user account accessible via the internet, such that the user (or medical professionals, etc.) may interface with logic contained within the electronics module 230 to tailor dosages and provide for permissions on dispensing the aerosol solution to the user.

The electronics module 230 may include a communications module capable of wirelessly communicating with the external user device and/or the data receiver 209, a battery to power its components, a memory device to store information specific to the user, as well as dosage and/or product information associated with the canister 202, and a processor (e.g., controller or microprocessor) to process dosage instructions and other data, and to provide instructions to the counter 210, the top cap 225, and/or other electronic components of the inhaler 200 as to any controls that should be placed on amounts to be dispensed of the solution within the currently installed canister. The communications module may include, for example, Bluetooth or other wireless technology for connecting to the user device.

In some cases, the electronics module 230 may also include an accelerometer to determine whether the solution has been properly prepared prior to dispensing. For example, the solution may be a blend that needs to be sufficiently shaken to uniformly mix an active component with a carrier component and be effective. Insufficient mixing may cause the blend to be too strong, too weak, or otherwise ineffective. The accelerometer may be configured to determine how hard and/or how long the canister 202 has been shaken by the user prior to actuation. The electronics module 230 may store information indicating minimum mixing thresholds (e.g., number of shakes, intensity of each shake, frequency of shakes, etc.) and may compare that information with the measurements obtained by the accelerometer to determine whether the solution is ready for dispensing. The inhaler 200 may also include an indicator 234 that is coupled to the electronics module 230 and configured to indicate when the solution is ready for use. For example, the indicator 234 may be an externally-visible LED light that turns on when the solution is ready, as shown in FIG. 3. In some embodiments, the indicator may include different colored lights, one color to indicate when the solution is not ready and needs more shaking, and another color to indicate when the solution is properly mixed. In one example embodiment, actuation of the canister 202 may be blocked until the solution is properly shaken by activating a lock, such as safety mechanism 231 described below.

As shown in FIGS. 4A and 4B, the lower body 218 of the inhaler 200 includes an electromechanical safety mechanism 231 configured to prevent users from over-dosing in a single day, or otherwise preventing use of the inhaler 200. The safety mechanism 231 may include a lock out feature or blocking mechanism that works in conjunction with the counter 210, the smart label 208, and the electronics module 230 (e.g., the processor included therein) to determine the maximum number of doses for a given day and track the number of doses being administered. Once the maximum number has been reached, the safety mechanism 231 may automatically activate the lock out feature. In one example embodiment, the lock out feature physically or mechanically prevents downward movement of the canister 202, thus preventing actuation of the converter and/or other aerosolization system. For example, the safety mechanism 231 may be a block or other rigid structure that can be automatically moved into or out of contact with a bottom surface 233 of the canister 202 to prevent or allow downward actuation of the canister 202, as shown in FIGS. 4A and 4B. In other embodiments, the safety mechanism 231 may include a lock out feature that electronically prevents actuation of the canister 202, as will be appreciated.

In some embodiments, the inhaler 200 also includes a child-proof lock 232 configured to prevent unwanted or accidental use of the inhaler 200 by a child. In some cases, the child-proof lock 232 is coupled to the electromechanical safety mechanism 231 to prevent actuation of the canister 202 and/or aerosolization system when the child lock 232 is activated. In such cases, the child-proof lock 232 and electromechanical safety mechanism 231 may collectively form a lock out system of the inhaler 200. As shown in FIG. 3, the child-lock 232 may be implemented as a button that, when pressed inwards, slides into a slot 235 formed in the side of the safety mechanism 231, as illustrated in FIG. 4A. While positioned within the slot 235, the child-lock button 232 activates the safety mechanism 231 by holding the safety mechanism 231, or block, in place, thus preventing downward motion of the canister 202. When the child-lock button 232 is deactivated, the button 232 extends out from the inhaler 200, thus moving clear of the path traveled by the safety mechanism 231 during downward actuation of the canister 202, as shown in FIG. 4B. For example, when the user presses downwards on the canister 202, the bottom surface 233 of the canister 202 also pushes the safety mechanism 231 downwards by the same distance, d. The safety mechanism 231 may include a spring mechanism that causes the block 231 to bounce back to a neutral position once the downward force is removed. In other embodiments, the child-lock 232 may include a twist-lock mechanism, for example, as shown in FIGS. 7A-7D. Other techniques may also be used to implement the child-proof and/or electromechanical lock out system, for example, as shown in FIGS. 13-24.

The inhalant dispensing system 201 described herein can be employed for a variety of practical uses. For example, the system 201 can track a user's consumption of certain solutions and prevent the user from overdosing or taking in more solution than is proscribed over a period of time. Contrarily, if a certain dosage is required to be administered, the system 201 can send an alert that it is time to take a dosage, or that the user has fallen behind in taking dosages. This alert could be sent, for example, to a user's smart watch or smartphone via Bluetooth or other near field wireless communication protocol. The information could also be stored and accessible by a reader used by medical professionals, or uploaded to the user's medical charts so that a medical professional can monitor dosaging and make adjustments remotely as necessary to the amount to be dispensed.

The system 201 can also be used to confirm the contents of the canister 202 installed in the inhaler 200, and report this to the user before the user inhales the aerosol solution. Content information and other data, such as the manufacturer, the location and date of solution fill, etc., can be stored on the RFID chip 208 attached to the canister 202 and thereby made available to the user. When presented, the data could be combined with information in a memory of the system 201 and/or the top cap 225 and processed to provide warnings or alerts to the user via a an application user interface on the user's smartphone, etc. These warnings could be simply based off of information within the RFID chip 208 (e.g., the solution has expired, the solution contains carcinogens, etc.), or it may be combined with data specific to the user stored within memory of the top cap 225 (e.g., the user has had bad reactions to this particular solution in the past, the user is allergic to a substance within this solution, or the user has marked and identified via the user interface that this is a solution that makes her or him drowsy, etc.).

Other optional features include indicative lighting and a user identification system. For example, lighting along a panel of the inhaler 200 (or the exposed surface of the canister 202) could be used to indicate an alert or dispensing problem to the user in an instant fashion, so that consultation with a separate user interface is not required. For example, a yellow light could indicate that a full dosage has been restricted for some reason, a red light could indicate a dosage is not presently available, and a green light indicates a full dosage has been dispensed. More information as to why a red or yellow light shows up could then be accessed via the user interface. A user identification system could be employed such as through use of a fingerprint reader on the inhaler 200. In this manner, the system 201 could confirm the user and access the appropriate user information stored within the memory of the system 201.

The canister 202 could also contain information about the solution's form, viscosity and blend of materials such as *cannabis* extracts, terpenes, nutraceuticals, essential oils, or cannabinoids, as well as information on appropriate usage, effectiveness, side effects, etc. The processor of the system 201 could use this information to adjust its heating temperature and other dispensing characteristics to maximize effectiveness of the solution. The system 201 could also convey information to the user about number of dosages left, and could automatically place an order for a new cartridge when dosage is running low.

FIGS. 7A-7D show an exemplary inhaler 300 that includes a twist-lock mechanism 332 for securing a canister 302 to the inhaler 200 and for preventing accidental use of the inhaler 300 as part of a child-lock feature or other lock-out system, in accordance with embodiments. A top cap 320, similar to the top cap 109 shown in FIG. 1A, may be secured to the canister 302 using a threaded mechanism (not shown) or other attachment mechanism, such that the two pieces move in unison within the inhaler 300. The inhaler 300 may be substantially similar to the inhaler 200, and the canister 302 may be substantially similar to the canister 202, except that an upper chamber 311 of the inhaler 300 includes a track system 334 for receiving one or more protrusions or buttons 336 included on lower, side surface(s) of the top cap 320 coupled to or over the canister 302. The track system 334 and the protrusion(s) 336 cooperate to form the twist-lock mechanism 332. In some cases, two protrusions 336 (not shown) located on opposite sides of the canister cap 320 may be configured to be aligned with and simultaneously received in vertical tracks 334a and 334b, respectively, located on opposite sides of the upper chamber 311. In other cases, the canister cap 320 includes only one protrusion 336, which may be coupled to either vertical track 334a or 334b of the inhaler 300.

Figure 7A:
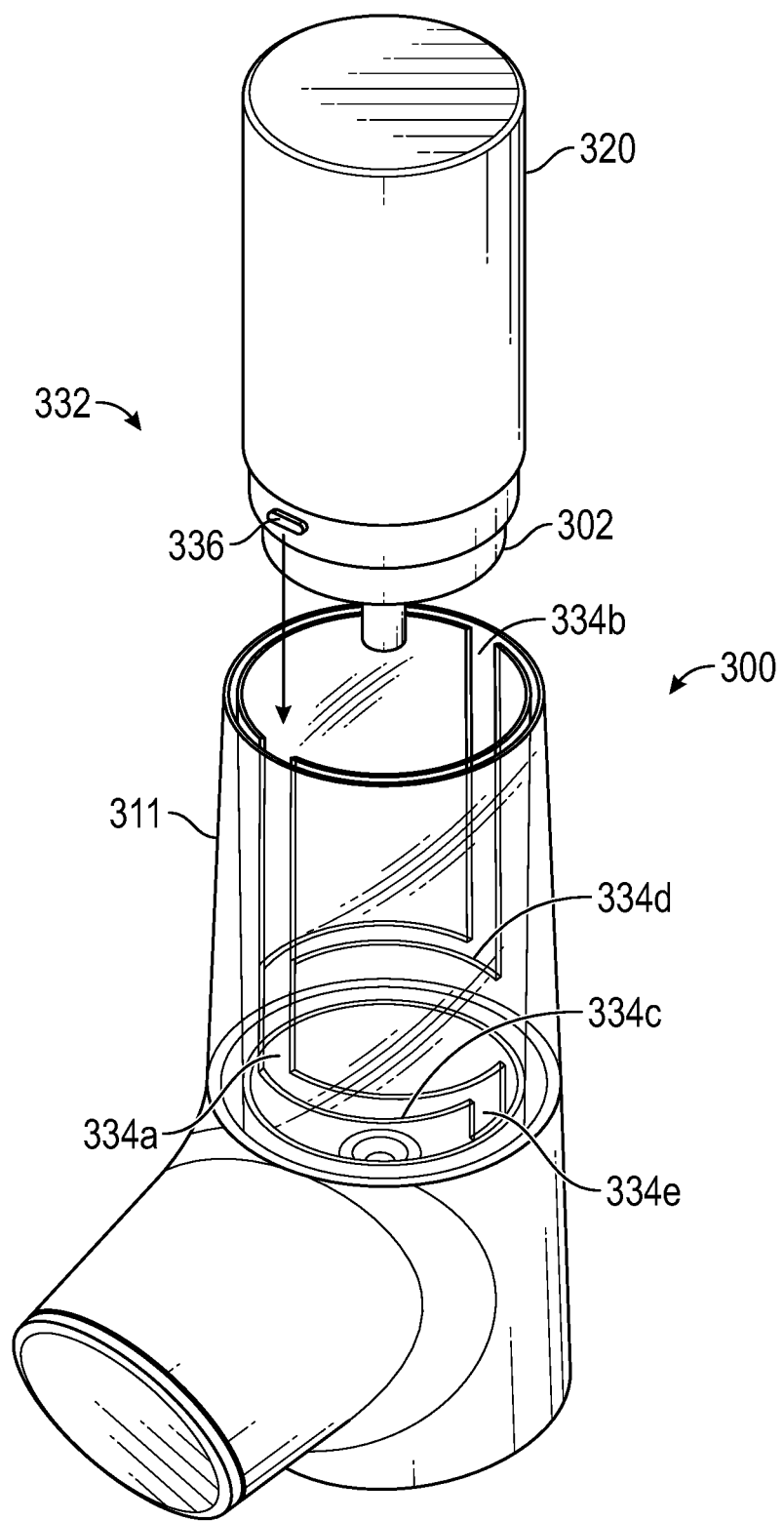
FIGS. 7A-7D are front perspective views of an exemplary inhalant dispenser showing a series of steps for installation of a smart canister, in accordance with certain embodiments.
Figure 7B:
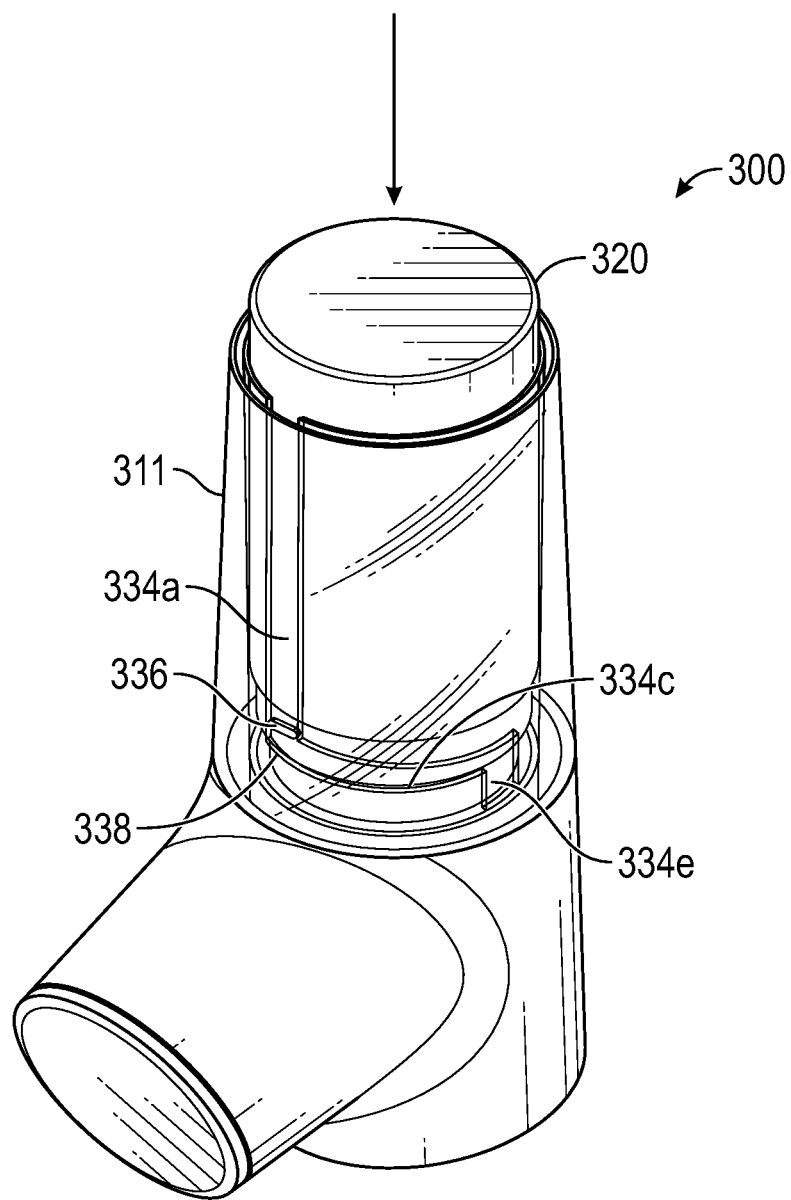

To install the canister 302 into the inhaler 300, the protrusion 336 is first aligned with an open end of the vertical track 334a or 334b and then dropped into the upper chamber 311, as shown in FIG. 7A. During this latter step, the protrusion 336 slides down the entire length of the vertical track 334a or 334b until it reaches a bottom wall 338 of the track system 334, as shown in FIG. 7B. While resting against the bottom wall 338, the protrusion 336 cannot be moved downwards, which means the canister 302 is also prevented from being pressed downwards, or otherwise actuating the convertor or other aerosolization system. The canister cap 320 remains locked in place so long as the protrusion 336 rests against bottom wall 338 of the track system 334. Thus, the inhaler 300 enters a locked position once the canister cap 320 is initially installed.

As shown in FIG. 7A, the track system 334 also includes horizontal tracks 334c and 334d, which are connected to and extend perpendicularly from, the vertical tracks 334a and 334b, respectively. As shown in FIG. 7B, the bottom wall 338 forms one wall of the horizontal track 334c. The track system 334 also includes a shorter vertical track 334e that extends below and perpendicularly from a far end of the horizontal track 334c. Though not shown, a similar shorter track may extend vertically below the horizontal track 334d, and a second bottom wall forms one wall of the horizontal track 334d.

Figure 7C:
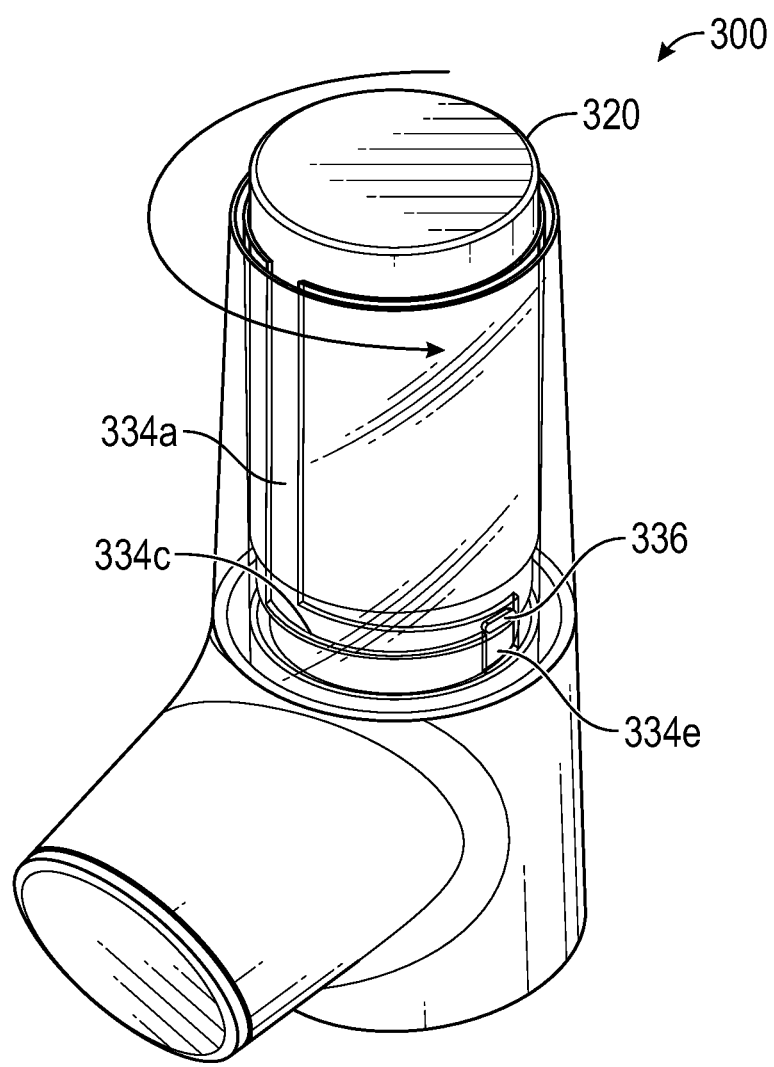
Figure 7D:
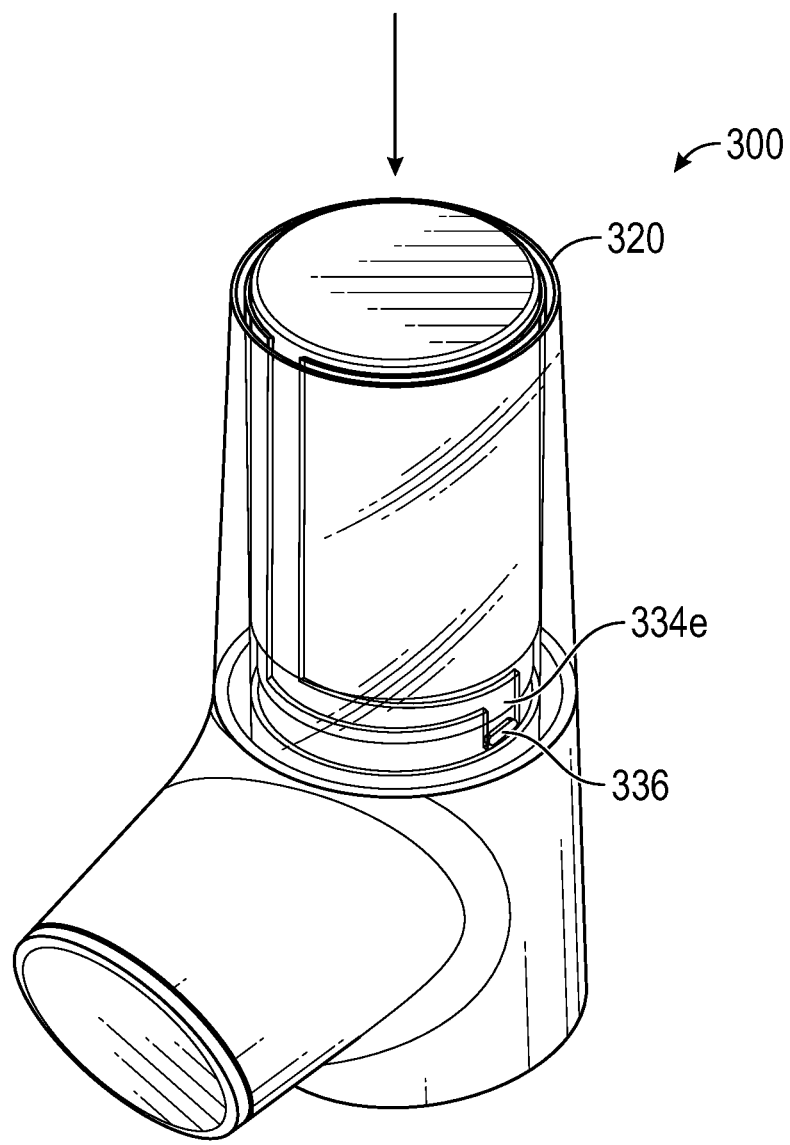

To unlock the inhaler 300, or move the canister cap 320 from the locked position to an unlocked position, the canister cap 320 is turned in a counterclockwise direction, as shown in FIG. 7C. The turning motion causes the protrusion 336 to be moved across the bottom wall 338 and through the horizontal track 334c. The turning motion (e.g., a quarter turn) may end once the protrusion 336 abuts or contacts an opposite end of the horizontal track 334c, thus placing the protrusion 336 in alignment with or directly above the shorter vertical track 334e, as shown in FIG. 7C. This placement enables the protrusion 336 to move downwards into the track 334e if the canister 302 is pressed down to actuate aerosolization of the canister solution, as shown in FIG. 7D. Thus, the inhaler 300 enters an unlocked position once the canister cap 320 is turned counterclockwise through the horizontal track 334c.

Once in the unlocked position or configuration, the inhaler 300 can be moved to a dispensing position and actuated, by pressing down on the canister cap 320 until the protrusion 336 travels to the bottom of the shorter vertical track 334e, as shown in FIG. 7D. Releasing the downward force on the canister 302 may cause the canister cap 320 to spring back up, so that the protrusion 336 travels up the shorter vertical track 334e and back into the horizontal track 334c. The inhaler 300 may be returned to the locked position or configuration by twisting or turning the canister cap 320 clockwise through the horizontal track 334c until the protrusion 336 is aligned with the vertical track 334a. The inhaler 300 may remain in this locked position between uses, thus providing the child-lock feature.

Figure 8:
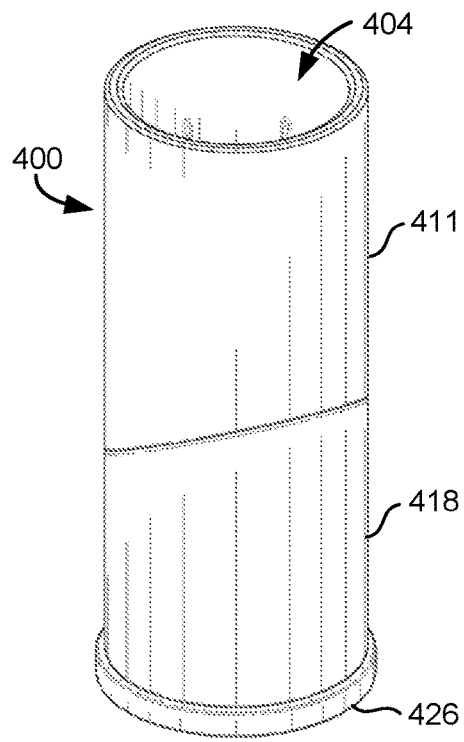
FIG. 8 is a perspective view of another exemplary inhalant dispenser, shown in a storage position, in accordance with certain embodiments.
Figure 9:
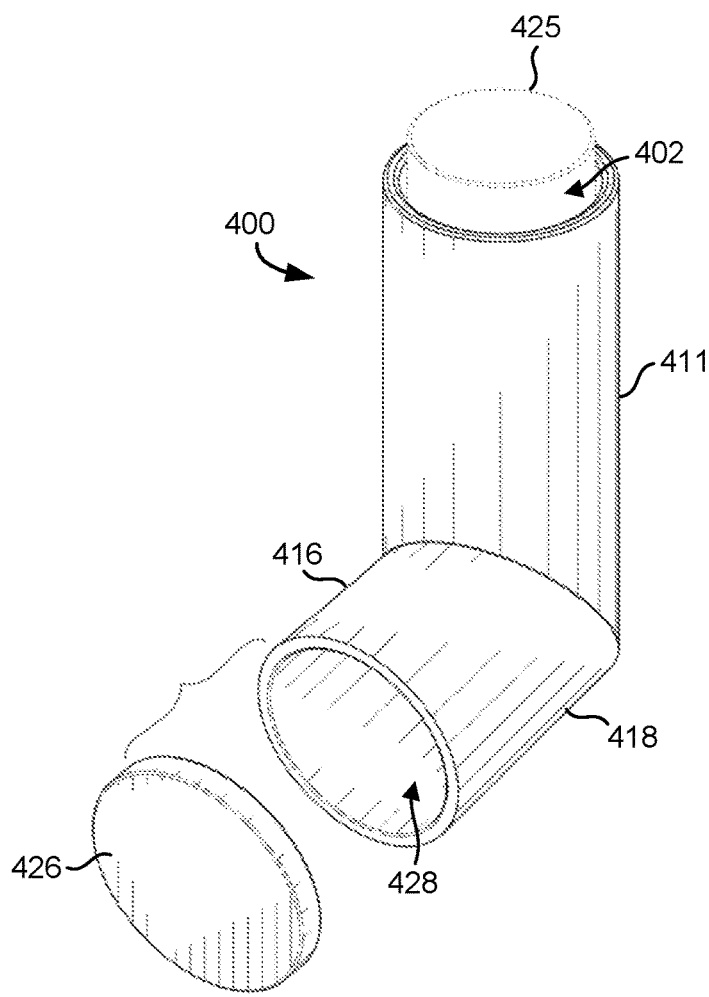
FIG. 9 is a partially exploded, perspective view of the inhalant dispenser of FIG. 8, but in a dispensing position and with an exemplary canister installed therein, in accordance with certain embodiments.
Figure 10:
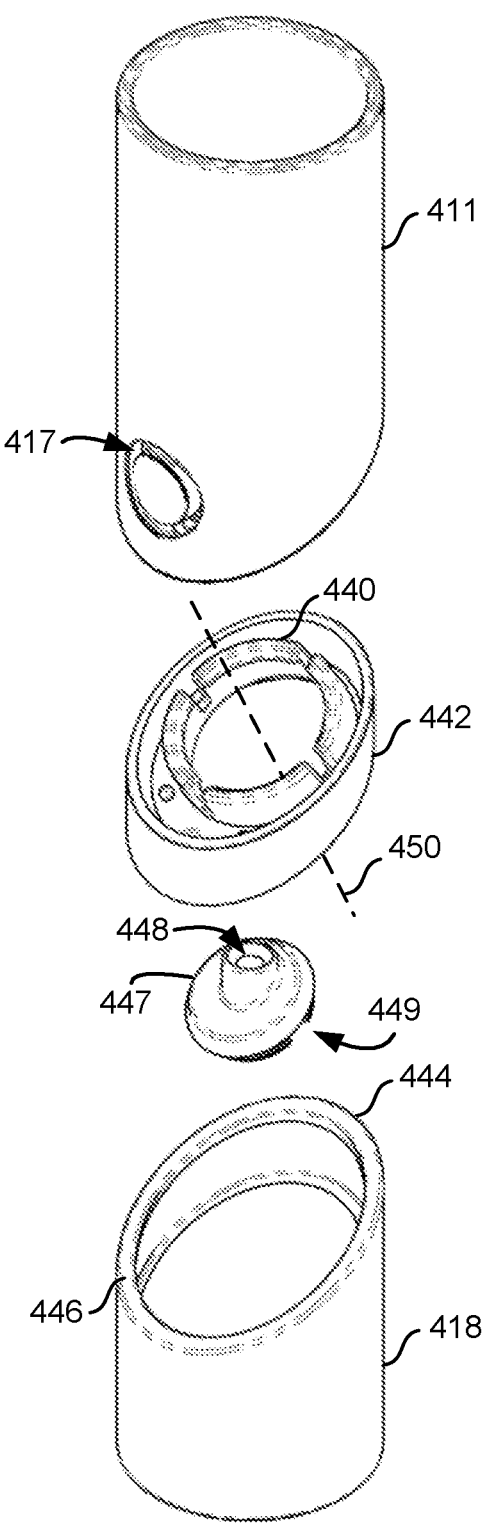
FIG. 10 is an exploded view of the inhalant dispenser shown in FIG. 8, in accordance with certain embodiments.
Figure 11:
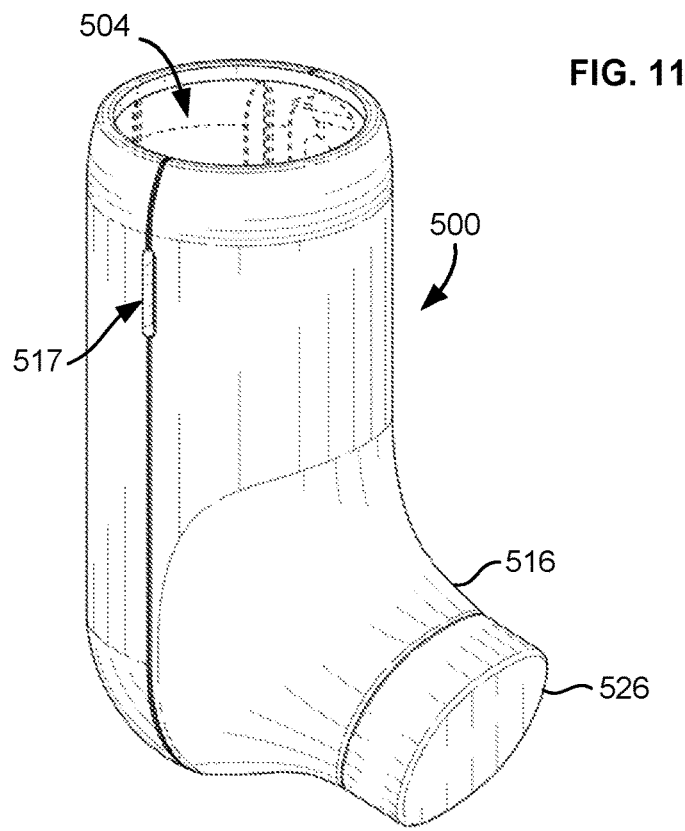
FIG. 11 is a perspective view of another exemplary inhalant dispenser, shown in an storage position, in accordance with certain embodiments.
Figure 12:
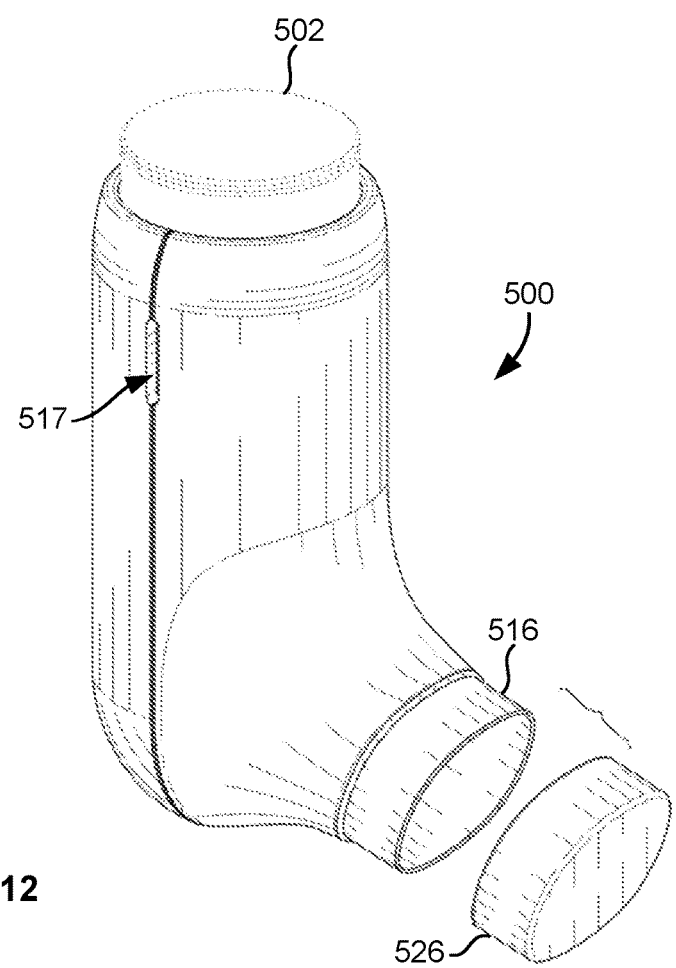
FIG. 12 is a partially exploded, perspective view of the inhalant dispenser shown in FIG. 11, but in a dispensing position and with an exemplary canister installed therein, in accordance with certain embodiments.

FIGS. 8-10 depict another exemplary inhalant device or inhaler 400, in accordance with some embodiments. FIGS. 11 and 12 depict yet another example inhalant device or inhaler 500, in accordance with other embodiments. Though not shown, each of the inhalers 400 and 500 may include one or more components of the inhalers 200 and/or 300. For example, the inhaler 400/500 may be configured to include the RFID/NFC reader 209, the electronics module 230, the safety mechanism 231, and/or the child-proof lock 232 described above and shown in FIG. 3B. As another example, the inhaler 400/500 may be configured to include the twist-lock mechanism 332 described above and shown in FIGS. 7A-7D.

Referring now to FIGS. 8-10, the inhaler 400 includes a twist mechanism that enables articulation of the body of the inhaler 400 between a storage position, wherein the upper and lower chambers 411 and 418 are vertically aligned such that the entire inhaler 400 is upright, as shown in FIG. 8, and a dispensing position, wherein a mouthpiece 416 of the inhaler 400 is articulated forward into an angled position, as shown in FIG. 9. The twist mechanism may include, for example, a joint 440 (also referred to herein as "moveable device") that movably or rotatably connects an upper chamber or body 411 of the inhaler 400 to a lower chamber or body 418 of the inhaler 400. As shown in FIG. 10, an internal chassis or collar 442 carries the joint 440 and may be coupled at least partially inside the upper chamber 411 and/or at least partially inside the lower chamber 418. The joint 440 and attached collar 442 may be snap-locked together at an angle and may be able to spin on an axis 450 that is perpendicular to both 440 and 442, but at an angle to the upper and lower chambers 411 and 418, as shown in FIG. 10. In embodiments, the joint 440 may include detents (not shown) or other physical markers to guide the articulation or rotation of the lower chamber 418 between the storage position (e.g., 0 degrees relative to the upper chamber 411) and the dispensing position (e.g., 90 degrees relative to the upper chamber 411). For example, the user may feel a click when the joint 440 engages one of the detents.

As shown in FIG. 8, the upper chamber 411 may meet the lower chamber 418 at a predetermined angle (e.g., 35 degrees). The upper and lower surfaces of the upper chamber 411 and lower chamber 418 may be angled accordingly to ensure a smooth fit, as shown in FIG. 10. In embodiments, the lower chamber 418 may be articulated about an axis formed by the meeting line between the two chambers. For example, when the lower chamber 418 is articulated upwards, an upper edge 444 of the lower chamber's upper surface moves inward, towards the internal collar 442, until it is hidden from view, as shown in FIG. 9. At the same time, a lower edge 446 of the lower chamber's upper surface remains in place against the lower surface of the upper chamber 411. As a result, the lower chamber 418 moves both inwards and upwards when articulated to the dispensing position.

The upper chamber 411 includes an open top 404 for receiving a smart canister 402 therein, as shown in FIG. 9. The canister 402 may be covered by or coupled to a top cap 425, similar to the top cap 225 described herein. A nozzle or valve actuator 447 may be included between the lower chamber 418 and upper chamber 411, adjacent the collar 442. In some embodiments, the nozzle 447 may be attached to a bottom end of the upper chamber 411, using a technique that is similar to the snap-lock attachment of the valve actuator 240 to the main body 211 of the inhaler 200. As shown in FIG. 10, the inhaler 400 may also include an air vent 417 in the upper chamber 411 for allowing air flow through the inhaler 400.

The nozzle 447 may be configured to receive a dispensing end of the canister 402 (e.g., dispensing end 206 shown in FIG. 2A) and cause the canister 402 to release a dose of solution upon actuation (e.g., when the user presses down on the canister 402 or presses a button for initiating actuation). For example, as shown in FIG. 10, the nozzle 447 includes an aperture 448 configured to receive the dispensing end of the canister 402. Though not shown, an internal portion of the nozzle 447 may be similar to the valve actuator 240 of inhaler 200 in terms of operation (e.g., aerosolization). For example, the nozzle 447 may include an internal channel (e.g., similar to internal channel 254 shown in FIG. 6D) that is communicatively coupled to the aperture 448 and configured to receive the dispensing end of the canister 402, and an expansion chamber (e.g., similar to expansion chamber 256 shown in FIG. 6D) that is communicatively coupled to the internal channel and configured to receive a dose of pressurized solution dispensed from the canister 402 upon actuation.

The lower chamber 418 forms the mouthpiece 416 of the inhaler 400 once the inhaler 400 is articulated to the dispensing position. As shown in FIG. 9, when in the dispensing position, an open end 428 of the mouthpiece 416 is angled to one side of the inhaler 400 (e.g., substantially perpendicular to the upper chamber 411). As shown in FIG. 10, a lower portion 449 of the nozzle 447 may also be angled to match the angle of the mouthpiece 416 when in the dispensing position, so that the aerosolized solution dispensed from the nozzle 447 is directed straight out the open end 428 of the mouthpiece 416. For example, the lower portion 449 may include an orifice (e.g., similar to the orifice 258 shown in FIGS. 6C and 6D) that is angled towards the open end 428 of the mouthpiece 416, when the mouthpiece 416 is in the dispensing position. The angle of the orifice is fixed, i.e. does not change when the lower chamber 418 is rotated. Thus, if the canister 402 is actuated while the inhaler 400 is in the storage position, the aerosol will be sprayed towards an interior wall of the lower chamber 418 and may not reach the open end 428. As shown in FIG. 8, the open end 428 may be covered by a cap 426 when the inhaler 400 is in the storage position.

In some embodiments, the canister 402 may have a smart label, similar to the smart label 110 described herein, attached to an outer surface of the canister 402. In some embodiments, the inhaler 400 further includes a safety-lock mechanism that prevents the lower chamber 418 from bending into the dispensing position, or otherwise locks the canister 402 from being used, if certain conditions are met, such as, e.g., maximum dosing amounts, or in response to activation of a child-lock or other safety mechanism.

Referring now to FIGS. 11 and 12, shown is another form of inhaler. The inhaler 500 has a smooth outer construction and more simple design, overall. Air vents 517 may be integrated into the sidewalls of the inhaler 500. A canister 502 may in inserted into an open end 504 of the inhaler 500, as shown in FIG. 12. A cap 526 may be removably coupled to a mouthpiece 516 of the inhaler 500 when not in use.

FIGS. 13-24 illustrates additional examples of a safety lock mechanism or lock out system that may be included in any inhaler or inhaler-type device that requires downward actuation of a canister disposed therein to dispense a dose of aerosolized solution from the canister to the user via a mouthpiece of the device. Each of the lock out systems described herein (including the twist-lock mechanism 332 shown in FIGS. 7A-7D and the electromechanical safety mechanism 231 and child-proof lock 232 shown in FIGS. 4A and 4B) is configured to prevent user inhalation of an aerosolized solution or other inhalant by preventing actuation of the canister, preventing usage of an inhalant delivery mechanism included in the inhaler, or otherwise blocking delivery of the inhalant to a mouthpiece of the inhaler. In most cases, the lock out system includes a movable mechanism or component that is selectively controlled via a user input or manipulation (i.e. manually). For example, the movable component may be rotatable between a first position and a second position, wherein the component is configured to prevent, or mechanically block, delivery of the aerosolized solution when disposed in the first position and permit delivery when displaced or disposed in the second position. In other cases, the lock out system can be configured to automatically control or limit usage of the inhaler in response to detecting a condition associated with the inhaler (e.g., exceeding a threshold for total number of doses dispensed within a given time period, etc.), as described herein. In the illustrated embodiments, the lock out systems are depicted in the inhaler 200, in place of the electromechanical safety mechanism 231 and/or child-proof lock 232 shown in FIGS. 4A and 4B. In other embodiments, the lock out systems may be implemented in any of the inhalers 400 and 500 with appropriate modifications to accommodate the different housing designs, as will be appreciated. Similarly, the lock out systems described herein may be implemented in any other type of inhaler.

Referring now to FIG. 13 and FIGS. 14A through 15B, shown is a first exemplary lock out system comprising a rotatable knob 600, in accordance with embodiments. An exterior portion 602 of the rotatable knob 600 is configured to form a user handle for manual manipulation or rotation of the knob 600. For example, as shown in FIG. 13, the exterior portion 602 may extend out from a back side of the main body 211 of the inhaler 200 by a distance that is sufficient to allow the user to grasp and/or turn the knob 600. An interior portion 604 of the rotatable knob 600 extends into an inner chamber 268 of the main body 211 and is configured to engage the canister 202 when the knob 600 is actuated. For example, the interior portion 604 can be configured to prevent vertical or downward movement of the canister 202 when the knob 600 is turned to a locked position, as shown in FIG. 14A, and can be configured to allow downward movement of the canister 202 when the knob 600 is turned to an unlocked position, as shown in FIG. 14B.

More specifically, in the illustrated embodiment, the interior portion 604 is positioned between the upper chamber 222 and lower chamber 220 of the inhaler main body 211 and is disposed adjacent to a bottom surface 270 of the top cap 225 of the canister 202. As shown in FIGS. 15A and 15B, the interior portion 604 forms a semi-circular protrusion with a curved edge 606 on one side and a flat edge 608 on an opposing side, adjacent to a cut out region 610. The interior portion 604 is configured such that when the rotatable knob 600 is in the locked position, the curved edge 606 faces upward and engages the bottom surface 270 of the canister's top cap 225, thus blocking the canister 202 from moving downwards or vertically, as shown in FIGS. 14A and 15A. As the rotatable knob 600 is turned to the unlocked position, the curved edge 606 rotates away from the bottom surface 270 until the flat edge 608 is substantially parallel to the bottom surface 270 of the canister top cap 225 and the cut-out region 610 faces the canister 202, as shown in FIGS. 14B and 15B. The cut-out region 610 can be configured to provide sufficient clearance or open space for the canister 202 to move downwards towards the valve actuator 240 and engage the same for dispensing purposes. For example, FIG. 14B shows the canister 202 in a dispensing position, wherein the base end 259 of the canister 202 is pressed against the top of the valve actuator 240 and the dispensing tube 212 is pushed upwards passed the movable barrier 264 and into the solution compartment 214, in order to release an amount of solution into the valve actuator 240 for aerosolization and dispensing.

FIGS. 16A through 18B illustrate a second exemplary lock out system 700, in accordance with embodiments. The second lock out system 700 includes a collar 702 configured to be attached to the canister 202, as shown in FIG. 18A, either permanently or removably, and a plurality of flexible beams 704 configured for installation within the main body 211 of the inhaler 200, as shown in FIGS. 16A and 16B. A bottom end of each flexible beam 704 may be attached to the base plate 244 of the valve actuator 240 within the inhaler 200, either permanently or removably, and a top end of each flexible beam 704 may be movably attached to the canister 202 upon installation of the canister 202 within the inhaler 200. The flexible beams 704 may be configured to stand rigid, or be inflexible, when pressed against by a downward force that is, for example, substantially perpendicular to the top of the beams 704. In addition, the beams 704 may be configured to flex or bend in response to a lateral force that is, for example, substantially perpendicular to the sides of the beams 704. As an example, the flexible beams 704 may be made of plastic or other suitable resilient material.

As shown in FIG. 18B, the collar 702 has a generally elliptical or almond shape with narrower portions 706 on opposite ends of the collar 702 and a wider or rounded midsection 708 there between. During use, the second lock out system 700 can be placed in a locked position by rotating the canister 202 so that the collar midsection 708 is positioned between the flexible beams 704, as shown in FIG. 17. In this position, the collar midsection 708 is disposed directly adjacent to the beams 704 without touching or pressing against the beams 704, and the beams 704 are pressed against the bottom surface 233 of the canister 202, thus allowing the flexible beams 704 to stand straight or at rest. To unlock the system 700, the canister 202 is rotated, either clockwise or counterclockwise, until the narrower portions 706 are pressed against the flexible beams 704, such that the beams 704 are forced outwards by the collar 702, as shown in FIG. 16A. In this unlocked position, the canister 202 is free to move downwards towards the valve actuator 240 in response to a downward actuation by the user, thus allowing the dispensing tube 212 to push past the moveable barrier 264 and enter the solution compartment, as shown in FIG. 16B. In embodiments, the beams 704 are flexible even to accommodate not only the full width of the collar 702 (i.e. the distance between the narrower portions 706) but also the bottom surface 233 of the canister 202 and portion thereof just above the bottom surface 233 (i.e. a bottom end of the cartridge 101 disposed within the canister 202). The beams 704 may also be configured to return to the neutral or at rest position shown in FIG. 17 once the lateral force exerted by the collar 702 and canister 202 is removed.

Figure 19A:
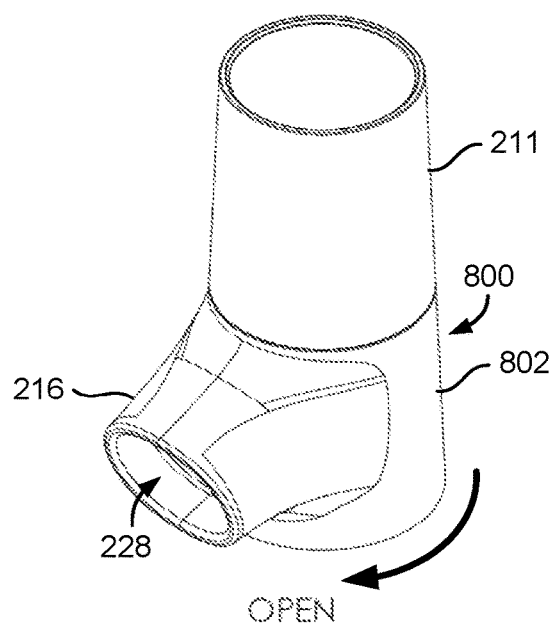
FIGS. 19A and 19B are front perspective views of an exemplary inhalant dispenser comprising a third lockout system, the third lockout system being shown in open and locked positions, respectively, in accordance with certain embodiments.
Figure 19B:
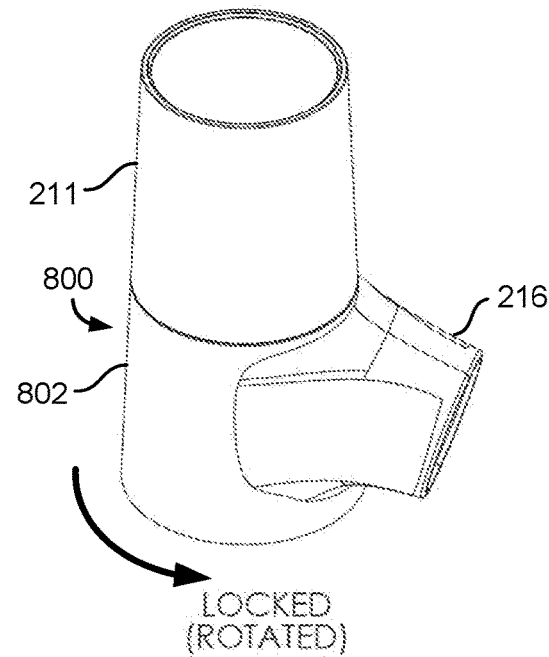
Figure 20A:
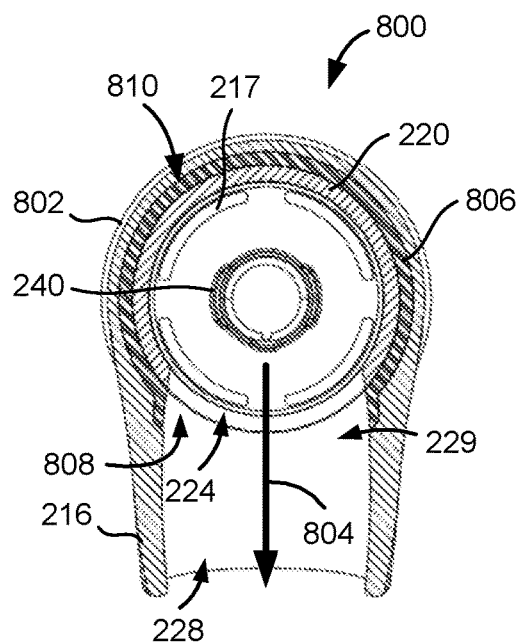
FIGS. 20A and 20B are transverse cross-sectional views of the inhalant dispenser of FIGS. 19A and 19B, respectively, in accordance with certain embodiments.
Figure 20B:
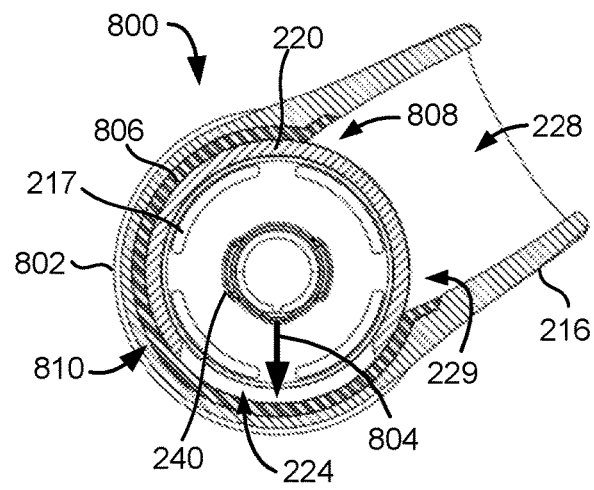

FIGS. 19A through 20B illustrate a third exemplary lock out system 800, in accordance with embodiments. The third lock out system 800 comprises a rotatable boot 802 that is substantially similar to the silicone boot 218 shown in FIG. 5 in terms of exterior design. For example, the rotatable boot 802 is coupled to the lower chamber 220 of the inhaler's main body 211, either permanently or removably, and includes the mouthpiece 216 for enabling user inhalation of an aerosol dispensed from the valve actuator 240. Internally, however, the boot 802 is rotatably coupled to the main body 211 of the inhaler 200, or more specifically, to the lower chamber 220 of the main body 211. Moreover, the boot 802 may be rotatable between a first, or open, position as shown in FIG. 19A, and a second, or locked, position as shown in FIG. 19B. The open position creates an open pathway 804 between the lower chamber 220 and the mouthpiece 216, via the aperture 224, thus allowing the aerosolized solution to flow from the valve actuator 240 directly into the mouthpiece 216 and exit out the open end 228 thereof, as shown in FIG. 20A. The locked position blocks or disrupts the pathway 804 between the aperture 224 and the mouthpiece 216, thus preventing the aerosol from exiting the lower chamber 220, as shown in FIG. 20B.

In embodiments, the third lock out system 800 further comprises a twist mechanism 806 configured to allow rotation of the boot 802 relative to the main body 211 in a first direction (e.g., towards the open position) and in a second direction, opposite the first (e.g., towards the locked position). The twist mechanism 806 may be coupled between the boot 802 and the lower chamber 220 and may be configured to glide against the lower chamber 220 to drive rotation of the boot 802. As shown in FIG. 20A, the twist mechanism 806 includes an opening 808 that aligns with the internal open end 229 of the mouthpiece 216 and with the aperture 224 when the boot 802 is in the open position. As the boot 802 rotates to the locked position, the opening 808 of the twist mechanism 806 travels with the boot 802 away from the aperture 224 and a solid wall portion 810 of the twist mechanism 806 moves in front of the aperture 224, thus blocking the aperture 224, as shown in FIG. 20B. The twist mechanism 806 may need to be rotated by at least a predetermined number of degrees in order to move the solid wall portion 810 to a position that fully covers the aperture 224 (e.g., 120 degrees). In some cases, the twist mechanism 806 may include stoppers (e.g., at 0 degrees and 120 degrees) to prevent rotation beyond the open position in the first direction and beyond the locked position in the second direction. In other cases, the twist mechanism 806 may be configured to enable 360 degree rotation of the boot 802 relative to the main body 211, and may include grooves or other components to tactilely indicate the locations of the open position and the locked position to the user during rotation.

Figure 21A:
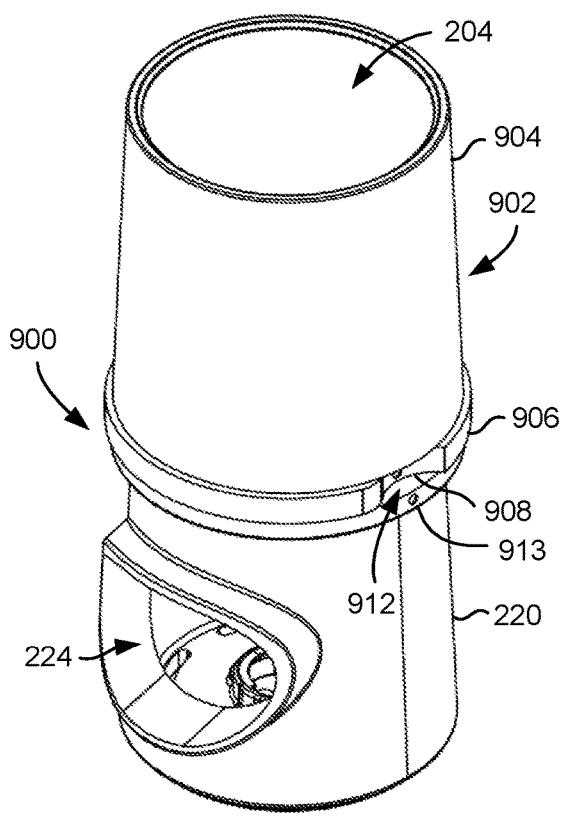
FIG. 21A is a perspective view of an interior portion of an exemplary inhalant dispenser comprising a fourth lockout system, the fourth lockout system shown in lock configuration, in accordance with certain embodiments.

FIGS. 21A through 22B illustrate a fourth exemplary lock out system 900, in according with embodiments. The fourth lock out system 900 comprises a main body 902 that is substantially similar to the main body 211 of the inhaler 200 shown in FIG. 5 in terms of overall functionality. For example, the main body 902 includes the open top 204 for receiving the canister 202 therein. The main body 902 also includes the lower chamber 220 with the aperture 224 and the valve actuator 240 coupled therein. The main body 902 further includes an upper chamber 904 that is generally similar to the upper chamber 222, except for a twist lock mechanism 906 coupled to a lower portion of the upper chamber 222 adjacent to the lower chamber 220, as shown in FIG. 21A.

Figure 21B:
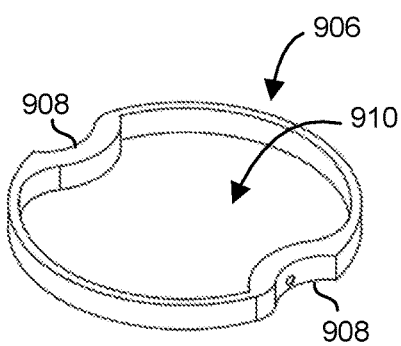
FIG. 21B is a close-up, perspective view of an exemplary ring of the fourth lockout system shown in FIG. 21A, in accordance with certain embodiments.
Figure 22A:
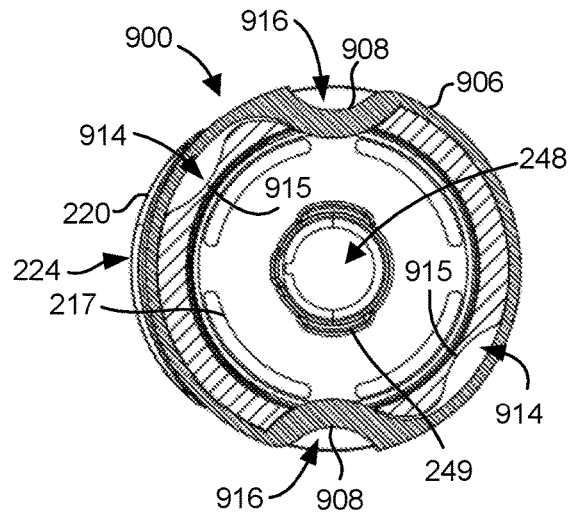
FIG. 22A is a transverse cross-sectional view of the interior portion shown in FIG. 21A, in accordance with certain embodiments
Figure 22B:
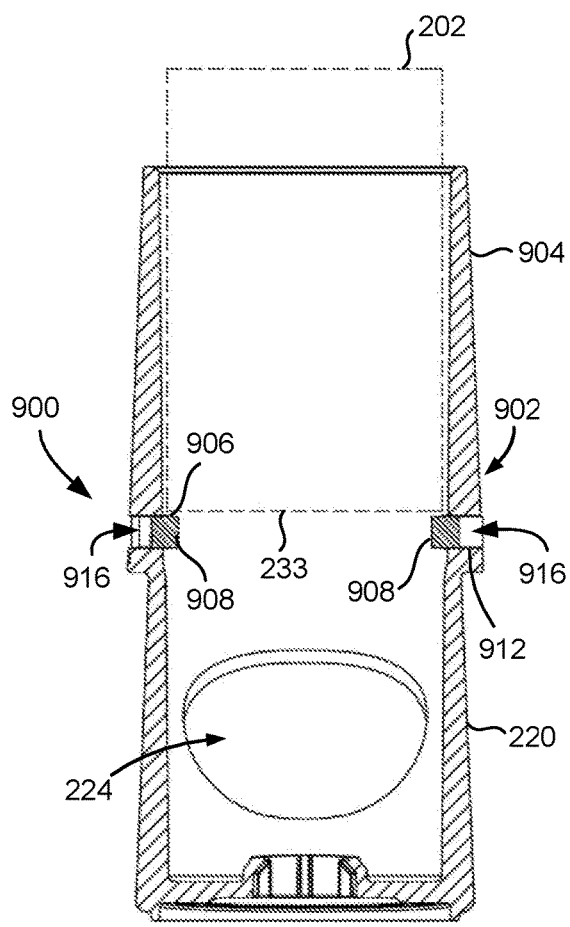
FIG. 22B is a lengthwise cross sectional view of the interior portion shown in FIG. 21A with an exemplary canister installed therein, in accordance with certain embodiments.

In embodiments, the twist lock mechanism 906 of the fourth lock out system 900 can be configured to block downward actuation or other downward movement of the canister 202 within the main body 902, thus preventing inhalation use of the inhaler 200. For example, as shown in FIG. 21B, the twist lock mechanism 906 may include a ring or annular disc with at least one notch 908 configured to reduce a diameter of the ring 906 in the area(s) containing the notch(es) 908. For example, in the illustrated embodiment, the twist ring 906 includes two notches 908 on opposing sides of the ring 906, such that the ring 906 is "pinched" in the middle, and each notch 908 is configured (e.g., sized and shaped) to curve inwards towards an open space 910 formed by the ring 906, thus reducing the ring diameter in the area between the two notches 908, as shown in FIGS. 21B and 22A. The size and shape of each notch 908 can be selected so that the reduced diameter between the notches 908 is smaller than a diameter of the canister 202, as shown in FIG. 22B. As a result, the canister 202 may be blocked from further downward movement once the bottom surface 233 of the canister 202 contacts or engages the notches 908 of the twist ring 906.

The fourth lock out system 900 further comprises a channel 912 formed in the upper chamber 904 of the main body 902, adjacent the lower chamber 220, for receiving the twist ring 906. The channel 912 can be configured to allow rotation of the twist ring 906 relative to the channel 912 and/or the main body 902. As shown in FIG. 22A, the channel 912 comprises a plurality of grooves 914, 916 for receiving the notches 908 as the twist ring 906 is rotated around the main body 902. The twist ring 906 may be made of a flexible plastic or other spring-like or resilient material capable of allowing the ring 906 to expand at least slightly when moving into a first set of grooves 914 and contract or spring back to a neutral state (e.g., shown in FIG. 21B) when moving into a second set of grooves 916.

In embodiments, the first set of grooves 914 may be configured to receive respective notches 908 when the fourth lock out system 900 is in an unlocked state, or when the canister 202 is free to move vertically within the main body 902. The first grooves 914 may be positioned within the channel 912 so that the grooves 914 do not extend into an inner region of the upper chamber 904, thus keeping the notches 908 out of the pathway of the canister 202. For example, as shown in FIG. 22A, the first grooves 914 are separated from the inner region of the upper chamber 904 by a solid wall 915 of the channel 912. The second set of grooves 916 may be configured to receive respective notches 908 when the fourth lock out system 900 is in a locked state, or when the canister 202 is prevented from downward movement. The second grooves 916 may be positioned within the channel 912 so that the grooves 916 extend into the inner region of the upper chamber 904, thus allowing the second grooves 916 to block the downward path of the canister 202. For example, as shown in FIG. 22A, the second grooves 916 align with two gaps in the channel wall 915 that are sized and shaped to allow the notches 908 to extend into the inner region of the upper chamber 904.

Figure 23A:
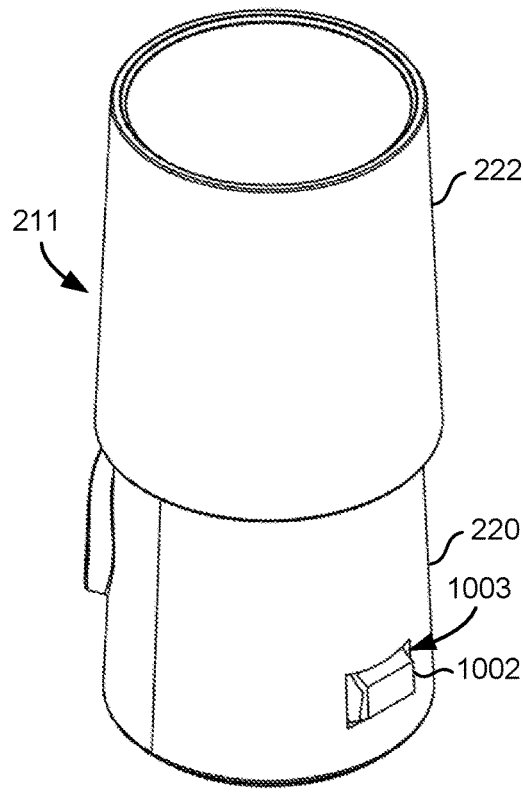
FIG. 23A is a rear perspective view of an exemplary inhalant dispenser comprising a fifth lockout system, in accordance with certain embodiments.
Figure 23B:
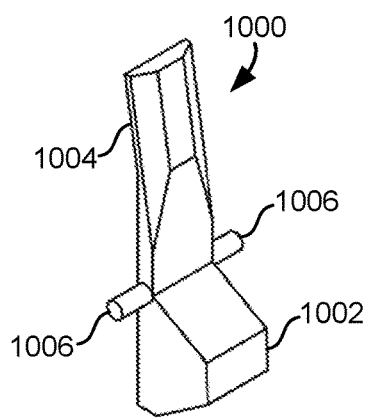
FIG. 23B is a close-up, perspective view of an exemplary toggle of the fifth lockout system, in accordance with certain embodiments.
Figure 24:
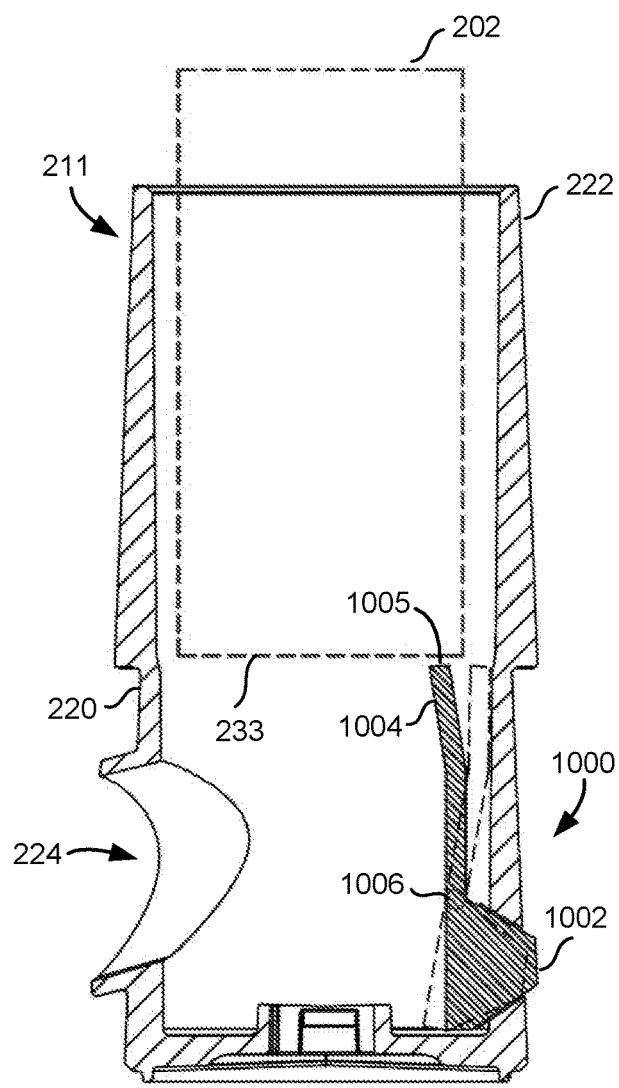
FIG. 24 is a lengthwise cross-sectional view of the inhalant dispenser of FIG. 23A with an exemplary canister installed therein, in accordance with certain embodiments.

FIGS. 23A through 24 illustrate a fifth exemplary lock out system 1000, in accordance with embodiments. The fifth lock out system 1000 is configured to prevent downward movement of the canister 202 when in a locked state and to allow downward movement of the canister 202 when in an unlocked state, as shown in FIG. 24. More specifically, the fifth lock out system 1000 comprises a rotatable or moveable toggle with a button portion 1002 that extends out from an opening 1003 in the sidewall of the lower chamber 220. The button portion 1002 may be used by the user to select the locked or unlocked position of the toggle 1000. For example, the user may press the button portion 1002 inwards in order to unlock the system 1000, or move an extended end 1004 of the toggle 1000 out of the downward pathway of the canister 202. In some embodiments, the button portion 1002 may be pressed again to lock the system 1000, or move the extended end 1004 of the toggle 1000 inward or into the pathway of the canister 202. For example, as shown in FIG. 24, the toggle 1000 may block the canister 202 from moving down into the lower chamber 220 by pressing a top end 1005 of the toggle 1000 against the bottom surface 233 of the canister 202.

The toggle 1000 further includes side levers 1006 configured to movably secure the toggle 1000 to the lower chamber 220. As shown in FIGS. 23B and 24, the side levers 1006 may extend substantially horizontally from opposing sides of the toggle 1000, thus forming an axis of rotation for the toggle 1000. For example, the toggle 1000 may rotate forward about the axis formed by the side levers 1006 when moving into the locked position and may rotate backwards about this axis when moving into the unlocked position. In some embodiments, the toggle 1000 may be a rocker switch that automatically springs into the locked position so long as the button portion 1002 is not being pressed by the user. In such cases, the user must continuously press the button portion 1002 while actuating the canister 202 and inhaling from the mouthpiece (not shown).

Thus, the techniques described herein provide an inhalant dispensing system for use in controlling and monitoring dosages of a solution contained within a smart canister and administered from the canister via an inhaler. The smart canister has controls in place to limit the amount of solution converted to aerosol and dispensed, and also contains and provides information about the solution itself. The system reads information stored on the canister and processes it along with information specific to a particular user to make dosage determinations, provide warnings, and update dosage information for monitoring and tracking purposes. The system also includes a safety mechanism for preventing accidental or unwanted usage of the canister and/or overdosing. Various embodiments of the inhaler design are also disclosed, as well as an exemplary assembly for one type of inhaler.

It will be understood by those skilled in the art that various changes may be made and equivalents may be substituted without departing from the scope of the novel and non-obvious techniques disclosed in this application. Therefore, it is intended that the novel teachings of the present invention not be limited to the particular embodiment disclosed, but that they will include all embodiments falling within the scope of the appended claims.

What is claimed is:
1. An inhalant dispenser assembly, comprising:
 a main body having an open top, a bottom surface, and a sidewall extending between the open top and the bottom surface, the sidewall forming a hollow interior and the bottom surface having a first aperture;
 an inhalant delivery mechanism comprising a base plate with a post extending from the base plate, the post configured to insert into the main body via the first aperture in the bottom surface, the post comprising a chamber configured to receive an amount of solution, and a nozzle coupled to the chamber and configured to dispense the amount of solution as an aerosol; and
 a lower body coupled to the main body and comprising a mouthpiece configured to deliver the aerosol to a user; and
 a plurality of vents formed in the bottom surface of the main body at a location below the mouthpiece, wherein the plurality of vents are positioned around the base plate of the inhalant delivery mechanism when the post is inserted into the main body via the first aperture.

2. The inhalant dispenser assembly of claim 1, wherein the main body includes an opening formed into the sidewall, the opening being aligned with the mouthpiece of the lower body to allow the aerosolized amount of solution to flow from the inhalant delivery mechanism to the mouthpiece for user inhalation.

3. The inhalant dispenser assembly of claim 1, wherein the post of the inhalant delivery mechanism further comprises a top opening configured to receive a dispensing tube of a canister containing a solution for user inhalation, the amount of solution being dispensed from the canister into the chamber via the dispensing tube.

4. The inhalant dispenser assembly of claim 1, wherein the open top and hollow interior of the main body are configured to receive a canister containing a solution for user inhalation, and the amount of solution is dispensed from the canister into the chamber of the inhalant delivery mechanism in response to an actuation of the canister by the user.

5. The inhalant dispenser assembly of claim 4, wherein the solution is stored under pressure in the canister, and the inhalant delivery mechanism converts the amount of solution dispensed into the chamber into aerosol by causing a release of the pressure as the amount of solution exits the nozzle.

6. The inhalant dispenser assembly of claim 4, wherein the sidewall of the main body is configured to seat against the canister so as to impede airflow through the open top.

7. The inhalant dispenser assembly of claim 1, further comprising a lockout, wherein the assembly has a locked configuration in which the lockout mechanically blocks the delivery of the aerosol to the mouthpiece, and an unlocked configuration in which the lockout is displaced so as to allow the delivery of the aerosol to the mouthpiece.

8. The inhalant dispenser assembly of claim 1, wherein the lower body comprises an annular vent that is configured to align with the plurality of vents formed in the bottom surface of the main body.

9. The inhalant dispenser assembly of claim 1, wherein a suction of air applied at the mouthpiece causes air from outside the assembly to be drawn through the plurality of vents formed in the bottom surface of the main body.

10. An inhalant dispensing system, comprising:
an inhalant delivery apparatus comprising:
a main body configured to at least partially receive a canister containing a solution for user inhalation, and having a bottom surface with a plurality of vents that allow entry of air from outside the inhalant delivery apparatus;
a lower body coupled to the main body and comprising a mouthpiece positioned above the plurality of vents, an inhalant delivery mechanism comprising:
a base plate seated against the bottom surface of the main body and surrounded by the plurality of vents; and
a post extending from the base plate into the main body, the post comprising a chamber configured to receive an amount of the solution from the canister upon user actuation of the canister, and a nozzle coupled to the chamber and configured to dispense the amount of solution as an aerosol directed towards the mouthpiece.

11. The inhalant dispensing system of claim 10, wherein the lower body comprises an annular vent that is configured to align with the plurality of vents formed in the bottom surface of the main body.

12. The inhalant dispensing system of claim 10, wherein the solution is stored under pressure in the canister, the inhalant delivery mechanism configured to aerosolize the amount of solution dispensed into the chamber by causing a release of the pressure as the amount of solution exits the nozzle.

13. The inhalant dispensing system of claim 10, further comprising: a lockout disposed at least partially within the main body and configured to prevent actuation of the canister when in a first position and permit actuation of the canister when in a second position.

14. The inhalant dispensing system of claim 13, wherein the lockout is rotatable between the first position and the second position.

15. The inhalant dispensing system of claim 13, wherein the lockout is manually moveable between the first position and the second position.

16. The inhalant dispensing system of claim 13, further comprising an electronics module configured to monitor use of the inhalant delivery apparatus and automatically control operation of the lockout based on the use of the inhalant delivery apparatus.

17. The inhalant dispensing system of claim 13, wherein the canister is actuated by pressing the canister further down into the main body, and the lockout is configured to prevent downward actuation of the canister when in the first position.

18. The inhalant dispensing system of claim 10, wherein the main body comprises an open top and a sidewall; wherein the sidewall is formed so as to impede air flow through the open top when the canister is received through the open top.

19. The inhalant dispensing system of claim 10, wherein a suction of air applied at the mouthpiece causes air from outside the inhalant delivery apparatus to be drawn through the plurality of vents formed in the bottom surface of the main body.

* * * * *